United States Patent
Brostoff et al.

(12) 
(10) Patent No.: US 6,464,978 B1
(45) Date of Patent: *Oct. 15, 2002

(54) VACCINATION AND METHODS AGAINST MULTIPLE SCLEROSIS RESULTING FROM PATHOGENIC RESPONSES BY SPECIFIC T CELL POPULATIONS

(75) Inventors: Steven W. Brostoff, Carlsbad; Darcy B. Wilson, La Jolla; Lawrence R. Smith, Cardiff; Daniel P. Gold, Del Mar; Dennis J. Carlo, Rancho Santa Fe, all of CA (US)

(73) Assignee: The Immune Response Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/055,006

(22) Filed: Apr. 29, 1993

Related U.S. Application Data

(63) Continuation-in-part of application No. 08/010,483, filed on Jan. 28, 1993, now abandoned, which is a continuation of application No. 07/530,229, filed on May 30, 1990, now abandoned, which is a continuation-in-part of application No. 07/382,085, filed on Jul. 18, 1989, now abandoned, and a continuation-in-part of application No. 07/382,086, filed on Jul. 18, 1989, now abandoned, which is a continuation-in-part of application No. 07/326,314, filed on Mar. 21, 1989, now abandoned.

(51) Int. Cl.$^7$ ............................................. A61K 39/395

(52) U.S. Cl. ........................... 424/154.1; 424/184.1; 424/185.1; 424/183.1; 530/300; 530/350; 530/387.9; 530/389.6; 530/391.3; 530/391.7; 435/6; 435/7.1

(58) Field of Search ..................... 424/184.1, 185.1, 424/154.1, 183.1; 530/300, 350, 387.9, 389.6, 391.3, 391.7; 435/6, 7.1

(56) References Cited

U.S. PATENT DOCUMENTS

| | | | |
|---|---|---|---|
| 4,634,590 A | 1/1987 | Cohen et al. | 424/88 |
| 4,886,743 A | 12/1989 | Hood et al. | 435/5 |
| 4,996,194 A | 2/1991 | Cohen et al. | 514/21 |
| 5,612,035 A | 3/1997 | Howell et al. | |
| 5,614,192 A | 3/1997 | Vandenbark | |
| 5,667,967 A | 9/1997 | Steinman et al. | |
| 5,776,459 A | 7/1998 | Vandenbark | |
| 5,837,246 A | 11/1998 | Howell et al. | |
| 5,840,304 A | 11/1998 | Davis et al. | |

FOREIGN PATENT DOCUMENTS

| | | | |
|---|---|---|---|
| EP | 0527199 | 2/1996 | |
| WO | WO-A-86/06413 | 11/1986 | |
| WO | WO 91/01133 | 7/1991 | A61K/31/00 |
| WO | WO 9306135 | 4/1993 | |

OTHER PUBLICATIONS

Maeda et al. Arth & Rheum 37:406–413, 1994.*
Vandenbark et al J. Neuro Res. 43:391–402, 1996.*
Desquenne–Clark et al PNAS 88:7219–7223, 1991.*
Wraith et al Cell 57:709–715, 1989.*
Brostoff in Mat & Peptide Therapy in AA 203–218, 1993.*
Padula et al. J Immunol 146:879–883, 1991.*
Urban et al. Cell 54:577–592, 1988.*
Sakai et al PNAS 85:8606–8612, 1988.*
Karin et al. J Exp Med 180:2227–2237, 1994.*
Stites et al. Basic & Clin Immunol p. 703, 1987.*
Borgato et al Clin & Exp Rheum. 15:475–479, 1997.*
Gold et al J Neuroimmunol. 76:29–38, 1997.*
Hafler, D. A. et al., Immunology today 17(4):152–159, "TCR usage in human and experimental demyelinating disease", Apr. 1996.*
Giegerich et al., "Diversity of T cell receptor α and β chain genes expressed by human T cells specific for similar myelin basic protein peptide/major histocompatibility complexes," *Eur. J. Immunol.* 22:753–758 (1992).
Li et al., "Allelic variations in the human T cell receptor Vβ6.7 gene products," *J. Exp. Med.* 171:221–230 (1990).
Li et al., "The genomic structure of human Vβ6 T cell antigen receptor genes," *J. Exp. Med.* 174:1537–1547 (1991).
Yan et al., "Specificity and T cell receptor β chain usage of a human collagen type II–reactive T cell clone derived from a healthy individual," *Eur. J. Immunol.* 22:51–56 (1992).
Ben–Nun et al., Vaccination against autoimmune encephalomyelitis with T–Lymphocyte line cells reactive against myelin basic protein. *Nature* 292:60–61 (1981).
Acha–Orbea et al., Limited heterogeneity of T cell receptors from lymphocytes mediating autoimmune encephalomyelitis allows specific immune intervention. *Cell* 54:263–273 (1988).

(List continued on next page.)

Primary Examiner—Patrick J. Nolan
Assistant Examiner—Gerald R. Ewoldt
(74) Attorney, Agent, or Firm—Campbell & Flores LLP

(57) ABSTRACT

The present invention provides vaccines and a means of vaccinating a mammal so as to prevent or control specific T cell mediated pathologies or to treat the unregulated replication of T cells. The vaccine is composed of a T cell receptor (TCR) or a fragment thereof corresponding to a TCR present on the surface of T cells mediating the pathology. The vaccine fragment can be a peptide corresponding to sequences of TCRs characteristic of the T cells mediating said pathology. The vaccine is administered to the mammal in a manner that induces an immunologically effective response so as to affect the course of the disease. The invention additionally provides specific β-chain variable regions of the T cell receptor, designated Vβ6.2/3, Vβ6.5, Vβ2, Vβ5.1, Vβ13 and Vβ7, which are central to the pathogenesis of multiple sclerosis (MS).

23 Claims, 4 Drawing Sheets

OTHER PUBLICATIONS

Urban et al., Restricted use of T cell receptor V genes in murine autoimmune encephalomyelitis raises possibilities for antibody therapy. *Cell* 54:577–592 (1988).

Owhashi and Heber–Katz, Protection from experimental allergic encephalomyelitis conferred by a monoclonal antibody directed against a shared idiotype on rate T cell receptors specific for myelin basic protein. *J. Exp. Med.* 168:2153–2164 (1988).

Burns et al., Both rat and mouse T cell receptors specific for the encephalitogenic determinant of myelin basic protein use similar V α and V β chain genes even though the major histocompatibility complex of encephalitogenic determinants being recognized are different. *J. Exp. Med.* 169:27–39 (1989).

Chluba et al., T cell receptor β chain usage in myelin basic protein–specific rat T lymphocytes. *Eur. J. Immunol.* 19:279–284 (1989).

Wucherpfennig et al., Shared human T cell receptor Vβusage to immunodominant regions of myelin basic protein. *Science* 248:1016–1019 (1990).

Kimura et al., Sequences and repertoire of the human T cell receptor α and β chain variable region genes in thymocytes. *Eur. J. Immunol.* 17:375–383 (1987).

Sedgwick, J., Long–term depletion of CD8+ T cells in vivo in the rat: no observed role for CD8+ (cytotoxic/suppressor) cells in the immunoregulation of experimental allergic encephalomyelitis. *Eur. J. Immunol.* 18:495–502 (1988).

Zamvil et al., Predominant expression of a T cell receptor Vβ gene subfamily in autoimmune encephalomyelitis, *J. Exp. Med.* 167:1586–1596 (1988).

Lider et al., Anti–idiotypic network induced by a T cell vaccination against experimental autoimmune encephalomyelitis. *Science* 239:181–183 (1988).

Sun et al., Suppression of a experimentally induced autoimmune encephalomyelitis by cytolytic T–T cell interactions. *Nature* 332:843–845 (1988).

Offner et al., Lymphocyte vaccination against experimental autoimmune encephalomyelitis: evaluation of vaccination protocols. *J. Neuro. Immunol.* 21:13–22 (1898).

Choi et al., Interaction of *Staphylococcus aureus* toxin "superantigens" with human T cells. *Proc. Natl., Acad. Sci. USA* 86:8941–8945 (1989).

White et al., The Vβ–specific superantigen staphylococcal enterotoxin B: stimulation of mature T cells and clonal deletion in neonatal mice. *Cell* 63:659–661 (1990).

Pullen et al., Identification of the region of T cell receptor β chain that interacts with the self–superantigen Mls–$1^a$. *Cell* 61:1365–1374 (1990).

Janeway, C., Self superantigens? *Cell* 63:659–661 (1990).

Marrack and Kappler, The staphylococcal enterotoxins and their relatives. *Science* 248:705–711 (1990).

Ross et al., Antibodies to synthetic peptides corresponding to variable–region first–framework segments of T cell receptors. *Immunol. Res.* 8:81–97 (1989).

Yanagi et al., A human T cell–specific cDNA clone encodes a protein having extensive homology to immunoglobulin chains. *Nature* 308:145–149 (1984).

Biddison et al., The germuline repertoire of T–cell receptor beta–chain genes in patients with multiple sclerosis. *Res. Immunol.* 140: 212–215 (1989).

Schluter et al., Antibodies to synthetic joining segment peptide of the T–cell receptor β–chain: serological cross–reaction between products of T–cell receptors genes, antigen binding T–cell receptors and immunoglobins. *Chem. Abstracts* 105(1):464, abstract No. 4767q (1986).

Howell et al., Vaccination against experimental allergic encephalomyelitis with T cell receptor peptides. *Science* 246(4930) :668–670 (1989).

Vandenbark et al., Immunization with a synthetic T–cellk receptor V–region peptide protects against experimental autoimmune encephalomyelitis. Letters to *Nature* 341:541–544 (1989).

Patten et al, Structure, expression and divergence of T–cell receptor β–chain variable regions, *Nature* 312:40–46 (1984).

Howell et al., Limited T–cell receptor β–chain heterogeneity among interleukin 2 receptor–positive synovial T cells suggests a role for superantigen in rheumatoid arthritis. *Proc. Natl. Acad. Sci. USA* 88:10921–10925 (1991).

\* cited by examiner

V beta

| % | 1 | 2 | 3 | 4 | 5.1 | 5.2 | 6 | 7.2 | 8.1 | 8.3 | 9 | 10 | 11 | 12.1 |
|---|---|---|---|---|-----|-----|---|-----|-----|-----|---|----|----|------|
| 70 |  | 1 |  |  |  |  | 2 |  |  |  |  |  |  |  |
| 60-69 |  |  |  |  |  |  |  |  |  |  |  |  |  |  |
| 50-59 |  | 1 |  |  |  |  | 1 |  |  |  |  |  |  |  |
| 40-49 |  |  |  |  | 2 |  | 2 |  |  |  |  |  |  |  |
| 30-39 |  |  |  |  | 2 |  | 2 | 1 |  |  |  |  |  |  |
| 20-29 |  | 4 | 1 | 1 |  | 1 | 6 |  |  |  |  | 2 |  |  |
| 10-19 | 1 | 5 | 4 | 2 | 4 | 2 | 11 | 1 | 5 |  |  | 2 |  | 6 |
| 5-9 | 2 | 16 | 11 | 4 | 7 | 1 | 9 | 7 | 5 | 2 | 5 | 1 | 1 | 10 |
| 0-4 | 36 | 12 | 23 | 32 | 24 | 35 | 6 | 30 | 29 | 37 | 30 | 38 | 38 | 23 |

Figure 1A

V beta

| % | 12.2 | 13 | 13.5 | 14 | 15 | 16 | 17 | 18 | 19 | 20 | 21.1 | 21.2 | 21.3 | 22 | 23 | 24 |
|---|------|----|------|----|----|----|----|----|----|----|------|------|------|----|----|----|
| 70 |  |  |  |  |  |  |  |  |  |  |  |  |  |  |  |  |
| 60-69 |  | 1 |  |  |  |  |  |  |  |  |  |  |  |  |  |  |
| 50-59 |  |  |  |  |  |  |  |  |  |  |  |  |  |  |  |  |
| 40-49 |  | 1 |  |  |  |  |  |  |  |  | 1 |  |  |  |  |  |
| 30-39 | 3 | 2 |  |  | 1 |  | 1 |  |  |  |  |  |  |  |  |  |
| 20-29 |  |  |  |  | 1 |  | 1 |  |  |  | 2 |  |  |  |  |  |
| 10-19 |  | 10 |  | 3 |  |  | 2 | 1 |  |  | 1 |  |  | 1 |  | 1 |
| 5-9 | 1 | 9 |  | 7 | 3 |  | 6 | 1 | 1 |  | 5 |  | 4 | 2 | 3 |  |
| 0-4 | 37 | 16 | 39 | 29 | 34 | 39 | 37 | 31 | 38 | 37 | 39 | 30 | 35 | 36 | 35 | 38 |

Figure 1B

|          |                                                                                              | SEQ ID NO. |
|----------|----------------------------------------------------------------------------------------------|------------|
|          | 1         10        20        30        40        50        60        70        80        90 |            |
|          | MGTRLLCWAALCLLGADHTGAGVSQTPSNKVTEKGKYVELRCDPISGHTALYWYRQSLGQGPEFLIYFQGTGAADDSGLPNDRFFAVRPEGSVSTLKIQRTERGDSAVYLCASS |            |
| HuVβ6.1  | MGTRLLCWAALCLLGADHTGAGVSQTPSNKVTEKGKYVELRCDPISGHTALYWYRQSLGQGPEFLIYFQGTGAADDSGLPNDRFFAVRPEGSVSTLKIQRTERGDSAVYLCASS | 12 |
| HuVβ6.2/3|......W.GE.T.........S.RY...AKR.QD.A...........VS.F..Q.A........T..NEAQL.K....S....E...........QQE............ | 13 |
| HuVβ6.4  |...S..W.GE.T.........S.RY...KR.QD.A............VS............T..NVEAQQ.K........S.E....I..T.....QR...M.R.AST | 14 |
| HuVβ6.5  | M------.........ADT....N.RH.I.KR.QN.TE.........E.NR........T......T..NEAQLEK.R.LS...S.E..K.L.....E......Q....M..... | 15 |
| 6.5b     |                                                                                              | 16 |
| HuVβ6.9  |.................N.RHNI.KR.QN.TE.........E.NR........T......T..NEAQLEK.R.LS...S.E..K.F.....E......Q....M..... | 17 |
| HuVβ6.7  |..........F.V.F.....S...........D...........L..........NS.P.K....S...S.E.TG........T.....QQE............ | 18 |
| 6.7b     |                                                                                              | 19 |
| HuVβ6.8  |...S....M........QEIS..HN.RH.I.KR.QN.TE.........E.NR.....NP......T..NEAQLEK...LS..IS.E..K.F.....E......Q....M..... | 20 |
| HuVβ6w1  |.................S.RY...KR.QD.T.........S.VT....Q.A........T..NVEAQPDK........S......S.E....I..T.....QR...M.R.... | 21 |

Figure 2A

```
           1         10        20        30        40        50        60        70        80        90
           *         *         *         *         *         *         *         *         *         *
HuVβ13-1   NAGVTQTPKFQVLKTGQSMTLQCAQDMNHEYMSWYRQDPGMGLRLIHYSVGAGITDQGEVPNGYNVSRSTTEDFPLRLLSAAPSQTSVYFCASS    22
HuVβ13-2   .........R..........L.....................Y..........E.T.AK...D......LKQN.L.G.E.............   23
HuVβ13-3   ..................................NS.Y..........Y.ASE.T.K......LNKRE.S..E.................   24
HuVβ13-4   ..............HI......GL.P.....R....A....K..D...N......E..................................   25
HuVβ13-5   I.I..A.TS.I.AA.RR...R.T..R.NA.Y....LL......NT.T.GK...D..S...AN.D....T.A..V.................   26
HuVβ13-6   --------------..T..N.Y..........K.Y..P....K...........................EL.....CL............   27

HuVβ2.1a   MLLLLLLLGLAGSGLGAVVSQHPSWVICKSGTSVKIECRSLDFQATTMFWYRQFPKQSLMLMATSNEGSKATYEQGVEKDKFLINHASLTLSTLTVTSAHPEDSSFYICSAR  28
   2.1b    ..........R..........................................................K....................   29
   2.1c    ..........R................................................................................   30

HuVβ5.1    MGSRLLCWVLLCLLGAGPVKAGVTQTPRYLIKTRGQQVTLSCSPISGHRSVSWYQQTPGQGLQFLFEYFSETQRNKGNFPGRFSGRQFSNSREMAVSTLELGDSALYLCASS  31
```

Figure 2B

| Patient: | Vβ | SEQ ID NO. | N/Dβ/N | SEQ ID NO. | Jβ | SEQ ID NO. |
|---|---|---|---|---|---|---|
| 82 | 7.1 | CASS | 58 | QVPEGAL | 45 | GYTFSGSGTRLTVV-1.2 | 32 |
| 88 | 7.1 | CASS | | QD EG | 46 | YEQYFGPGTRLTVT-2.7 | 33 |
| 95 | 7.2 | CASS | | RHGRA | 47 | SYNEQFFGPGTRLTVL-2.1 | 34 |

| Patient: | Vβ3 | | N/Dβ/N | SEQ ID NO. | Jβ | SEQ ID NO. | NOTES |
|---|---|---|---|---|---|---|---|
| 81 | 7.2 | CASS | QUGGVA | 48 | GELFFGEGSRLTVL-2.2 | 35 | CD3+CD25+ |
|  | 7.2 | CASS | QEEHGG | 49 | TDTQYFGPGTRLTVL-2.3 | 36 | " |
|  | 7.2 | CASS | QDLTG | 50 | YNSPLHFGNGTRLTVT-1.6 | 37 | " |
|  | 7.3 | CASS | QDSVAY | 51 | SGNTIYFGEGSWLTVV-1.3 | 38 | " |
| 88 | 7.2 | CASS | QDRN | 52 | NEQFFGPGTRLTVL-2.1 | 39 | CD4+CD25+ |
|  | 7.1 | CAS | QDRRVD | 53 | EAFFGQGTRLTVV-1.1 | 40 | " |
|  | 7.2 | CASS | QDGTGW | 54 | QPQHFGDGTRLSIL-1.5 | 41 | " |
|  | 7.2 | CAS | HGTSGIL | 55 | ETQYFGPGTRLLVL-2.5 | 42 | " |
|  | 7.2 | CASS | QGWG | 56 | TQYFGPGTRLLVL-2.5 | 43 | " |
| 66 | 7.1 | CASS | QVAARPG | 57 | ELFFGEGSRLTVL-2.2 | 44 | DIRECT SORT CD3+CD25+ |

Figure 3

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
       (A) LENGTH: 8 amino acids
       (B) TYPE: amino acid
       (D) TOPOLOGY: unknown (ii) MOLECULE TYPE: peptide (xi) SEQUENCE DESCRIPTION: SEQ ID NO: 1:

Ser Gly Asp Gln Gly Gly Asn Glu
1            5

(2) INFORMATION FOR SEQ ID NO: 2:

(i) SEQUENCE CHARACTERISTICS:
       (A) LENGTH: 9 amino acids
       (B) TYPE: amino acid
       (D) TOPOLOGY: unknown (ii) MOLECULE TYPE: peptide (xi) SEQUENCE DESCRIPTION: SEQ ID NO: 2:

Ser Gly Asp Ala Gly Gly Gly Tyr Glu
1            5

(2) INFORMATION FOR SEQ ID NO: 3:

(i) SEQUENCE CHARACTERISTICS:
       (A) LENGTH: 8 amino acids
       (B) TYPE: amino acid
       (D) TOPOLOGY: unknown (ii) MOLECULE TYPE: peptide (xi) SEQUENCE DESCRIPTION: SEQ ID NO: 3:

Ser Ser Asp Ser Ser Asn Thr Glu
1            5

(2) INFORMATION FOR SEQ ID NO: 4:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (xi) SEQUENCE DESCRIPTION: SEQ ID NO: 4:

```
Ser Gly Asp Ala Gly Gly Tyr Glu
1               5
```

(2) INFORMATION FOR SEQ ID NO: 5:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO: 5:

```
Cys Ala Ser Ser Asp Ser Ser Asn Thr Glu Val Phe Phe Gly Lys
1               5                   10                  15
```

(2) INFORMATION FOR SEQ ID NO: 6:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO: 6:

```
Cys Ala Ser Ser Asp Ser Gly Asn Thr Glu Val Phe Phe Gly Lys
1               5                   10                  15
```

(2) INFORMATION FOR SEQ ID NO: 7:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO: 7:

```
Cys Ala Ser Ser Asp Ser Gly Asn Val Leu Tyr Phe Gly Glu Gly Ser
1               5                   10                  15
Arg
```

(2) INFORMATION FOR SEQ ID NO: 8:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO: 8:

```
Ala Ser Ser Asp Ser Ser Asn Thr Glu
1               5
```

(2) INFORMATION FOR SEQ ID NO: 9:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO: 9:

```
Asp Met Gly His Gly Leu Arg Leu Ile His Tyr Ser Tyr Asp Val Asn
1               5                   10                  15
Ser Thr Glu Lys
            20
```

(2) INFORMATION FOR SEQ ID NO: 10:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO: 10:

```
Arg Phe Gly Ala Gly Thr Arg Leu Thr Val Lys
1               5                   10
```

(2) INFORMATION FOR SEQ ID NO: 11:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO: 11:

```
Leu Gly Gln Gly Pro Glu Phe Leu Thr Tyr Phe Gln Asn Glu Ala Gln
1               5                   10                  15
Leu Glu Lys Ser
            20
```

(2) INFORMATION FOR SEQ ID NO: 12:

(i) SEQUENCE CHARACTERISTICS:
        (A) LENGTH: 114 amino acids
        (B) TYPE: amino acid
        (D) TOPOLOGY: unknown (ii) MOLECULE TYPE: protein (xi) SEQUENCE DESCRIPTION: SEQ ID NO: 12:

```
Met Gly Thr Arg Leu Leu Cys Trp Ala Ala Leu Cys Leu Leu Gly Ala
1               5                   10                  15
Asp His Thr Gly Ala Gly Val Ser Gln Thr Pro Ser Asn Lys Val Thr
            20                  25                  30
Glu Lys Gly Lys Tyr Val Glu Leu Arg Cys Asp Pro Ile Ser Gly His
        35                  40                  45
Thr Ala Leu Tyr Trp Tyr Arg Gln Ser Leu Gly Gln Gly Pro Glu Phe
    50                  55                  60
Leu Ile Tyr Phe Gln Gly Thr Gly Ala Ala Asp Asp Ser Gly Leu Pro
65                  70                  75                  80
```

Asn Asp Arg Phe Phe Ala Val Arg Pro Glu Gly Ser Val Ser Thr Leu
                    85                  90                  95

Lys Ile Gln Arg Thr Glu Arg Gly Asp Ser Ala Val Tyr Leu Cys Ala
                100                 105                 110

Ser Ser (2) INFORMATION FOR SEQ ID NO: 13:

(i) SEQUENCE CHARACTERISTICS:
        (A) LENGTH: 114 amino acids
        (B) TYPE: amino acid
        (D) TOPOLOGY: unknown (ii) MOLECULE TYPE: protein (xi) SEQUENCE DESCRIPTION: SEQ ID NO: 13:

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
                20                  25                  30

Lys Arg Gly Gln Asp Val Ala Leu Arg Cys Asp Pro Ile Ser Gly His
                35                  40                  45

Val Ser Leu Phe Trp Tyr Gln Gln Ala Leu Gly Gln Gly Pro Glu Phe
50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
                100                 105                 110

Ser Ser (2) INFORMATION FOR SEQ ID NO: 14:

(i) SEQUENCE CHARACTERISTICS:
        (A) LENGTH: 114 amino acids
        (B) TYPE: amino acid
        (D) TOPOLOGY: unknown (ii) MOLECULE TYPE: protein (xi) SEQUENCE DESCRIPTION: SEQ ID NO: 14:

Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
                20                  25                  30

Lys Arg Gly Gln Asp Val Ala Leu Arg Cys Asp Pro Ile Ser Gly His
                35                  40                  45

Val Ser Leu Tyr Trp Tyr Arg Gln Ala Leu Gly Gln Gly Pro Glu Phe
50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
                100                 105                 110

Ser Thr (2) INFORMATION FOR SEQ ID NO: 15:

(i) SEQUENCE CHARACTERISTICS:
        (A) LENGTH: 106 amino acids
        (B) TYPE: amino acid
        (D) TOPOLOGY: unknown (ii) MOLECULE TYPE: protein (xi) SEQUENCE DESCRIPTION: SEQ ID NO: 15:

```
Met Ala Leu Cys Leu Leu Gly Ala Asp His Ala Asp Thr Gly Val Ser
1               5                  10                  15

Gln Asn Pro Arg His Lys Ile Thr Lys Arg Gly Gln Asn Val Thr Phe
                20                  25                  30

Arg Cys Asp Pro Ile Ser Glu His Asn Arg Leu Tyr Trp Tyr Arg Gln
            35                  40                  45

Thr Leu Gly Gln Gly Pro Glu Phe Leu Thr Tyr Phe Gln Asn Glu Ala
        50                  55                  60

Gln Leu Glu Lys Ser Arg Leu Leu Ser Asp Arg Phe Ser Ala Glu Arg
65                  70                  75                  80

Pro Lys Gly Ser Leu Ser Thr Leu Glu Ile Gln Arg Thr Glu Gln Gly
                85                  90                  95

Asp Ser Ala Met Tyr Leu Cys Ala Ser Ser
            100                 105
```

(2) INFORMATION FOR SEQ ID NO: 16:

(i) SEQUENCE CHARACTERISTICS:
        (A) LENGTH: 106 amino acids
        (B) TYPE: amino acid
        (D) TOPOLOGY: unknown (ii) MOLECULE TYPE: protein (xi) SEQUENCE DESCRIPTION: SEQ ID NO: 16:

```
Met Ala Leu Cys Leu Leu Gly Ala Asp His Ala Asp Thr Gly Val Ser
1               5                  10                  15

Gln Asn Pro Arg His Lys Ile Thr Lys Arg Gly Gln Asn Val Thr Phe
                20                  25                  30

Arg Cys Asp Pro Ile Ser Glu His Asn Arg Leu Tyr Trp Tyr Arg Gln
            35                  40                  45

Thr Leu Gly Gln Gly Pro Glu Phe Leu Thr Tyr Phe Gln Asn Glu Ala
        50                  55                  60

Gln Leu Glu Lys Ser Arg Leu Leu Ser Asp Arg Phe Ser Ala Glu Arg
65                  70                  75                  80

Pro Lys Gly Ser Phe Ser Thr Leu Glu Ile Gln Arg Thr Glu Gln Gly
                85                  90                  95

Asp Ser Ala Met Tyr Leu Cys Ala Ser Ser
            100                 105
```

(2) INFORMATION FOR SEQ ID NO: 17:

(i) SEQUENCE CHARACTERISTICS:
        (A) LENGTH: 93 amino acids
        (B) TYPE: amino acid
        (D) TOPOLOGY: unknown (ii) MOLECULE TYPE: protein (xi) SEQUENCE DESCRIPTION: SEQ ID NO: 17:

Gly Val Ser Gln Asn Pro Arg His Asn Ile Thr Lys Arg Gly Gln Asn

| 1 | | | | 5 | | | | | 10 | | | | | 15 | |
|---|---|---|---|---|---|---|---|---|---|---|---|---|---|---|---|

Val Thr Phe Arg Cys Asp Pro Ile Ser Glu His Asn Arg Leu Tyr Trp
            20            25            30

Tyr Arg Gln Thr Leu Gly Gln Gly Pro Glu Phe Leu Thr Tyr Phe Gln
      35            40            45

Asn Glu Ala Gln Leu Glu Lys Ser Arg Leu Leu Ser Asp Arg Phe Ser
50            55            60

Ala Glu Arg Pro Lys Gly Ser Phe Ser Thr Leu Glu Ile Gln Arg Thr
65           70           75           80

Glu Gln Gly Asp Ser Ala Met Tyr Leu Cys Ala Ser Ser
         85           90

(2) INFORMATION FOR SEQ ID NO: 18:

(i) SEQUENCE CHARACTERISTICS:
        (A) LENGTH: 114 amino acids
        (B) TYPE: amino acid
        (D) TOPOLOGY: unknown (ii) MOLECULE TYPE: protein (xi) SEQUENCE DESCRIPTION: SEQ ID NO: 18:

Met Gly Thr Arg Leu Leu Phe Trp Val Ala Phe Cys Leu Leu Gly Ala
1           5            10            15

Asp His Thr Gly Ala Gly Val Ser Gln Ser Pro Ser Asn Lys Val Thr
         20             25            30

Glu Lys Gly Lys Asp Val Glu Leu Arg Cys Asp Pro Ile Ser Gly His
      35            40            45

Thr Ala Leu Tyr Trp Tyr Arg Gln Ser Leu Gly Gln Gly Leu Glu Phe
     50            55           60

Leu Ile Tyr Phe Gln Gly Asn Ser Ala Pro Asp Lys Ser Gly Leu Pro
65           70           75           80

Ser Asp Arg Phe Ser Ala Glu Arg Thr Gly Gly Ser Val Ser Thr Leu
         85             90           95

Thr Ile Gln Arg Thr Gln Gln Glu Asp Ser Ala Val Tyr Leu Cys Ala
      100           105          110

Ser Ser (2) INFORMATION FOR SEQ ID NO: 19:

(i) SEQUENCE CHARACTERISTICS:
        (A) LENGTH: 114 amino acids
        (B) TYPE: amino acid
        (D) TOPOLOGY: unknown (ii) MOLECULE TYPE: protein (xi) SEQUENCE DESCRIPTION: SEQ ID NO: 19:

Met Gly Thr Arg Leu Leu Phe Trp Val Ala Phe Cys Leu Leu Gly Ala
1           5            10            15

Asp His Thr Gly Ala Gly Val Ser Gln Ser Pro Ser Asn Lys Val Thr
         20             25            30

Glu Lys Gly Lys Asp Val Glu Leu Arg Cys Asp Pro Ile Ser Gly His
      35            40            45

Thr Ala Leu Tyr Trp Tyr Arg Gln Ser Arg Gly Gln Gly Arg Glu Phe
     50            55           60

Leu Ile Tyr Phe Gln Gly Asn Ser Ala Pro Asp Lys Ser Gly Leu Pro
65           70           75           80

```
Ser Asp Arg Phe Ser Ala Glu Arg Thr Gly Glu Ser Val Ser Thr Leu
                85                  90                  95

Glu Ile Gln Arg Thr Gln Gln Glu Asp Ser Ala Val Tyr Leu Cys Ala
                100                 105                 110

Ser Ser (2) INFORMATION FOR SEQ ID NO: 20:

(i) SEQUENCE CHARACTERISTICS:
        (A) LENGTH: 114 amino acids
        (B) TYPE: amino acid
        (D) TOPOLOGY: unknown (ii) MOLECULE TYPE: protein (xi) SEQUENCE DESCRIPTION: SEQ ID NO: 20:

Met Gly Thr Ser Leu Leu Cys Trp Met Ala Leu Cys Leu Leu Gly Ala
1               5                   10                  15

Asp Gln Glu Ile Ser Gly Val Ser His Asn Pro Arg His Lys Ile Thr
                20                  25                  30

Lys Arg Gly Gln Asn Val Thr Phe Arg Cys Asp Pro Ile Ser Glu His
                35                  40                  45

Asn Arg Leu Tyr Trp Tyr Arg Gln Asn Pro Gly Gln Gly Pro Glu Phe
50                  55                  60

Leu Thr Tyr Phe Gln Asn Glu Ala Gln Leu Glu Lys Ser Gly Leu Leu
65                  70                  75                  80

Ser Asp Arg Ile Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
                100                 105                 110

Ser Ser (2) INFORMATION FOR SEQ ID NO: 21:

(i) SEQUENCE CHARACTERISTICS:
        (A) LENGTH: 94 amino acids
        (B) TYPE: amino acid
        (D) TOPOLOGY: unknown (ii) MOLECULE TYPE: protein (xi) SEQUENCE DESCRIPTION: SEQ ID NO: 21:

Ala Gly Val Ser Gln Thr Pro Ser Asn Arg Tyr Thr Glu Lys Lys Arg
1               5                   10                  15

Tyr Gln Asp Leu Thr Cys Asp Pro Ile Ser Gly His Ser Ala Val Thr
                20                  25                  30

Trp Tyr Arg Gln Gln Leu Ala Gln Gly Pro Glu Phe Leu Ile Tyr Thr
            35                  40                  45

Gln Gly Asn Tyr Glu Ala Gln Pro Asp Lys Leu Pro Asn Asp Ser Phe
50                  55                  60

Phe Ala Ser Arg Glu Glu Gly Ser Val Ser Ile Leu Lys Ile Thr Arg
65                  70                  75                  80

Thr Glu Arg Gly Gln Arg Ala Val Tyr Met Cys Arg Ser Ser
                85                  90

(2) INFORMATION FOR SEQ ID NO: 22:

(i) SEQUENCE CHARACTERISTICS:
        (A) LENGTH: 94 amino acids
        (B) TYPE: amino acid
```

(D) TOPOLOGY: unknown (ii) MOLECULE TYPE: protein (xi) SEQUENCE DESCRIPTION: SEQ ID NO: 22:

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Glu Asp Phe Pro Leu Arg Leu Leu Ser
65                  70                  75                  80

Ala Ala Pro Ser Gln Thr Ser Val Tyr Phe Cys Ala Ser Ser
                85                  90
```

(2) INFORMATION FOR SEQ ID NO: 23:

(i) SEQUENCE CHARACTERISTICS:
      (A) LENGTH: 94 amino acids
      (B) TYPE: amino acid
      (D) TOPOLOGY: unknown (ii) MOLECULE TYPE: protein (xi) SEQUENCE DESCRIPTION: SEQ ID NO: 23:

```
Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Gly Glu Gly Thr Thr Ala Lys Gly Glu Val Pro Asp Gly Tyr
    50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys Ala Ser Ser
                85                  90
```

(2) INFORMATION FOR SEQ ID NO: 24:

(i) SEQUENCE CHARACTERISTICS:
      (A) LENGTH: 94 amino acids
      (B) TYPE: amino acid
      (D) TOPOLOGY: unknown (ii) MOLECULE TYPE: peptide (xi) SEQUENCE DESCRIPTION: SEQ ID NO: 24:

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Asn Ser Met
            20                  25                  30

Tyr Trp Tyr Arg Gln Asp Pro Gly Met Gly Leu Arg Leu Ile Tyr Tyr
        35                  40                  45

Ser Ala Ser Glu Gly Thr Thr Asp Lys Gly Glu Val Pro Asn Gly Tyr
    50                  55                  60

Asn Val Ser Arg Leu Asn Lys Arg Glu Phe Ser Leu Arg Leu Glu Ser
```

```
                  65                  70                  75                  80
Ala Ala Pro Ser Gln Thr Ser Val Tyr Phe Cys Ala Ser Ser
                            85                  90

(2) INFORMATION FOR SEQ ID NO: 25:

(i) SEQUENCE CHARACTERISTICS:
        (A) LENGTH: 94 amino acids
        (B) TYPE: amino acid
        (D) TOPOLOGY: unknown (ii) MOLECULE TYPE: protein (xi) SEQUENCE DESCRIPTION: SEQ ID NO: 25:

Asn Ala Gly Val Thr Gln Thr Pro Lys Phe His Ile Leu Lys Thr Gly
 1               5                  10                  15

Gln Ser Met Thr Leu Gln Cys Ala Gln Asp Met Asn His Gly Tyr Leu
                20                  25                  30

Ser Trp Tyr Pro Gln Asp Pro Gly Met Gly Leu Arg Arg Ile His Tyr
            35                  40                  45

Ser Val Ala Ala Gly Ile Thr Asp Lys Gly Glu Val Pro Asp Gly Tyr
        50                  55                  60

Asn Val Ser Arg Ser Asn Thr Glu Asp Phe Pro Leu Arg Leu Glu Ser
65                  70                  75                  80

Ala Ala Pro Ser Gln Thr Ser Val Tyr Phe Cys Ala Ser Ser
                            85                  90

(2) INFORMATION FOR SEQ ID NO: 26:

(i) SEQUENCE CHARACTERISTICS:
        (A) LENGTH: 94 amino acids
        (B) TYPE: amino acid
        (D) TOPOLOGY: unknown (ii) MOLECULE TYPE: protein (xi) SEQUENCE DESCRIPTION: SEQ ID NO: 26:

Ile Ala Gly Ile Thr Gln Ala Pro Thr Ser Gln Ile Leu Ala Ala Gly
 1               5                  10                  15

Arg Arg Met Thr Leu Arg Cys Thr Gln Asp Met Arg His Asn Ala Met
                20                  25                  30

Tyr Trp Tyr Arg Gln Asp Leu Gly Leu Gly Leu Arg Leu Ile His Tyr
            35                  40                  45

Ser Asn Thr Ala Gly Thr Thr Gly Lys Gly Glu Val Pro Asp Gly Tyr
        50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser
                            85                  90

(2) INFORMATION FOR SEQ ID NO: 27:

(i) SEQUENCE CHARACTERISTICS:
        (A) LENGTH: 77 amino acids
        (B) TYPE: amino acid
        (D) TOPOLOGY: unknown (ii) MOLECULE TYPE: protein (xi) SEQUENCE DESCRIPTION: SEQ ID NO: 27:

Ser Met Thr Leu Gln Cys Thr Gln Asp Met Asn His Asn Tyr Met Tyr
 1               5                  10                  15
```

```
Trp Tyr Arg Gln Asp Pro Gly Met Gly Leu Lys Leu Ile Tyr Tyr Ser
            20                  25                  30

Val Pro Ala Gly Ile Thr Asp Lys Gly Glu Val Pro Asn Gly Tyr Asn
            35                  40                  45

Val Ser Arg Ser Thr Thr Glu Asp Phe Pro Leu Arg Leu Glu Leu Ala
            50                  55                  60

Ala Pro Ser Gln Thr Cys Leu Tyr Phe Cys Ala Ser Ser
 65                 70                  75
```

(2) INFORMATION FOR SEQ ID NO: 28:

(i) SEQUENCE CHARACTERISTICS:
        (A) LENGTH: 112 amino acids
        (B) TYPE: amino acid
        (D) TOPOLOGY: unknown (ii) MOLECULE TYPE: protein (xi) SEQUENCE DESCRIPTION: SEQ ID NO: 28:

```
Met Leu Leu Leu Leu Leu Leu Gly Leu Ala Gly Ser Gly Leu Gly
 1               5                  10                  15

Ala Val Val Ser Gln His Pro Ser Trp Val Ile Cys Lys Ser Gly Thr
            20                  25                  30

Ser Val Lys Ile Glu Cys Arg Ser Leu Asp Phe Gln Ala Thr Thr Met
            35                  40                  45

Phe Trp Tyr Arg Gln Phe Pro Lys Gln Ser Leu Met Leu Met Ala Thr
            50                  55                  60

Ser Asn Glu Gly Ser Lys Ala Thr Tyr Glu Gln Gly Val Glu Lys Asp
 65                 70                  75                  80

Lys Phe Leu Ile Asn His Ala Ser Leu Thr Leu Ser Thr Leu Thr Val
                    85                  90                  95

Thr Ser Ala His Pro Glu Asp Ser Ser Phe Tyr Ile Cys Ser Ala Arg
                100                 105                 110
```

(2) INFORMATION FOR SEQ ID NO: 29:

(i) SEQUENCE CHARACTERISTICS:
        (A) LENGTH: 112 amino acids
        (B) TYPE: amino acid
        (D) TOPOLOGY: unknown (ii) MOLECULE TYPE: protein (xi) SEQUENCE DESCRIPTION: SEQ ID NO: 29:

```
Met Leu Leu Leu Leu Leu Leu Gly Leu Ala Gly Ser Gly Leu Gly
 1               5                  10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
            35                  40                  45

Phe Trp Tyr Arg Gln Phe Pro Lys Lys Ser Leu Met Leu Met Ala Thr
            50                  55                  60

Ser Asn Glu Gly Ser Lys Ala Thr Tyr Glu Gln Gly Val Glu Lys Asp
 65                 70                  75                  80

Lys Phe Leu Ile Asn His Ala Ser Leu Thr Leu Ser Thr Leu Thr Val
                    85                  90                  95

Thr Ser Ala His Pro Glu Asp Ser Phe Tyr Ile Cys Ser Ala Arg
                100                 105                 110
```

(2) INFORMATION FOR SEQ ID NO: 30:

(i) SEQUENCE CHARACTERISTICS:
        (A) LENGTH: 112 amino acids
        (B) TYPE: amino acid
        (D) TOPOLOGY: unknown (ii) MOLECULE TYPE: protein (xi) SEQUENCE DESCRIPTION: SEQ ID NO: 30:

```
Met Leu Leu Leu Leu Leu Leu Gly Leu Ala Gly Ser Gly Leu Gly
1               5                   10                  15

Ala Val Val Ser Gln His Pro Ser Arg Val Ile Cys Lys Ser Gly Thr
                20                  25                  30

Ser Val Lys Ile Glu Cys Arg Ser Leu Asp Phe Gln Ala Thr Thr Met
            35                  40                  45

Phe Trp Tyr Arg Gln Phe Pro Lys Gln Ser Leu Met Leu Met Ala Thr
50                      55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Arg
                100                 105                 110
```

(2) INFORMATION FOR SEQ ID NO: 31:

(i) SEQUENCE CHARACTERISTICS:
        (A) LENGTH: 114 amino acids
        (B) TYPE: amino acid
        (D) TOPOLOGY: unknown (ii) MOLECULE TYPE: protein (xi) SEQUENCE DESCRIPTION: SEQ ID NO: 31:

```
Met Gly Ser Arg Leu Leu Cys Trp Val Leu Leu Cys Leu Leu Gly
1               5                   10                  15

Ala Gly Pro Val Lys Ala Gly Val Thr Gln Thr Pro Arg Tyr Leu Ile
                20                  25                  30

Lys Thr Arg Gly Gln Gln Val Thr Leu Ser Cys Ser Pro Ile Ser Gly
            35                  40                  45

His Arg Ser Val Ser Trp Tyr Gln Gln Thr Pro Gly Gln Gly Leu Gln
50                      55                  60

Phe Leu Phe Glu Tyr Phe Ser Glu Thr Gln Arg Asn Lys Gly Asn Phe
65                  70                  75                  80

Pro Gly Arg Phe Ser Gly Arg Gln Phe Ser Asn Ser Arg Ser Glu Met
                85                  90                  95

Asn Val Ser Thr Leu Glu Leu Gly Asp Ser Ala Leu Tyr Leu Cys Ala
                100                 105                 110

Ser Ser
```

(2) INFORMATION FOR SEQ ID NO: 32:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 32:

```
Gly Tyr Thr Phe Ser Gly Ser Gly Thr Arg Leu Thr Val Val
1               5                   10
```

(2) INFORMATION FOR SEQ ID NO: 33:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 33:

```
Tyr Glu Gln Tyr Phe Gly Pro Gly Thr Arg Leu Thr Val Thr
1               5                   10
```

(2) INFORMATION FOR SEQ ID NO: 34:

(i) SEQUENCE CHARACTERISTICS:
        (A) LENGTH: 16 amino acids
        (B) TYPE: amino acid
        (D) TOPOLOGY: unknown (ii) MOLECULE TYPE: peptide (xi) SEQUENCE DESCRIPTION: SEQ ID NO: 34:

```
Ser Tyr Asn Glu Gln Phe Phe Gly Pro Gly Thr Arg Leu Thr Val Leu
1               5                   10                  15
```

(2) INFORMATION FOR SEQ ID NO: 35:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 35:

```
Gly Glu Leu Phe Phe Gly Glu Gly Ser Arg Leu Thr Val Leu
1               5                   10
```

(2) INFORMATION FOR SEQ ID NO: 36:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (xi) SEQUENCE DESCRIPTION: SEQ ID NO: 36:

```
Thr Asp Thr Gln Tyr Phe Gly Pro Gly Thr Arg Leu Thr Val Leu
1               5                   10                  15
```

(2) INFORMATION FOR SEQ ID NO: 37:

(i) SEQUENCE CHARACTERISTICS:
        (A) LENGTH: 16 amino acids
        (B) TYPE: amino acid
        (D) TOPOLOGY: unknown (ii) MOLECULE TYPE: peptide (xi) SEQUENCE DESCRIPTION: SEQ ID NO: 37:

```
Tyr Asn Ser Pro Leu His Phe Gly Asn Gly Thr Arg Leu Thr Val Thr
1               5                   10                  15
```

(2) INFORMATION FOR SEQ ID NO: 38:

(i) SEQUENCE CHARACTERISTICS:
        (A) LENGTH: 16 amino acids
        (B) TYPE: amino acid
        (D) TOPOLOGY: unknown (ii) MOLECULE TYPE: peptide (xi) SEQUENCE DESCRIPTION: SEQ ID NO: 38:

```
Ser Gly Asn Thr Ile Tyr Phe Gly Glu Gly Ser Trp Leu Thr Val Val
1               5                   10                  15
```

(2) INFORMATION FOR SEQ ID NO: 39:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 39:

```
Asn Glu Gln Phe Phe Gly Pro Gly Thr Arg Leu Thr Val Leu
1               5                   10
```

(2) INFORMATION FOR SEQ ID NO: 40:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 40:

```
Glu Ala Phe Phe Gly Gln Gly Thr Arg Leu Thr Val Val
1               5                   10
```

(2) INFORMATION FOR SEQ ID NO: 41:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 41:

```
Gln Pro Gln His Phe Gly Asp Gly Thr Arg Leu Ser Ile Leu
1               5                   10
```

(2) INFORMATION FOR SEQ ID NO: 42:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO: 42:

```
Glu Thr Gln Tyr Phe Gly Pro Gly Thr Arg Leu Leu Val Leu
1               5                   10
```

(2) INFORMATION FOR SEQ ID NO: 43:

(i) SEQUENCE CHARACTERISTICS:

(A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 43:

Thr Gln Tyr Phe Gly Pro Gly Thr Arg Leu Leu Val Leu
1               5                  10

(2) INFORMATION FOR SEQ ID NO: 44:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 44:

Glu Leu Phe Phe Gly Glu Gly Ser Arg Leu Thr Val Leu
1               5                  10

(2) INFORMATION FOR SEQ ID NO: 45:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (xi) SEQUENCE DESCRIPTION: SEQ ID NO: 45:

Gln Val Pro Glu Gly Ala Leu
1               5

(2) INFORMATION FOR SEQ ID NO: 46:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO: 46:

Gln Asp Glu Gly
1

(2) INFORMATION FOR SEQ ID NO: 47:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO: 47:

Arg His Gly Arg Ala
1               5

(2) INFORMATION FOR SEQ ID NO: 48:

(i) SEQUENCE CHARACTERISTICS:
        (A) LENGTH: 6 amino acids
        (B) TYPE: amino acid
        (D) TOPOLOGY: unknown

```
    (ii) MOLECULE TYPE: peptide (xi) SEQUENCE DESCRIPTION: SEQ ID NO: 48:

Gln Glu Gly Gly Val Ala
1               5

(2) INFORMATION FOR SEQ ID NO: 49:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO: 49:

Gln Glu Glu His Gly Gly
1               5

(2) INFORMATION FOR SEQ ID NO: 50:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO: 50:

Gln Asp Leu Thr Gly
1               5

(2) INFORMATION FOR SEQ ID NO: 51:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO: 51:

Gln Asp Ser Val Ala Tyr
1               5

(2) INFORMATION FOR SEQ ID NO: 52:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO: 52:

Gln Asp Arg Asn
1

(2) INFORMATION FOR SEQ ID NO: 53:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO: 53:
```

```
Gln Asp Arg Arg Val Asp
1               5
```

(2) INFORMATION FOR SEQ ID NO: 54:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO: 54:

```
Gln Asp Gly Thr Gly Trp
1               5
```

(2) INFORMATION FOR SEQ ID NO: 55:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (xi) SEQUENCE DESCRIPTION: SEQ ID NO: 55:

```
His Gly Thr Ser Gly Ile Leu
1               5
```

(2) INFORMATION FOR SEQ ID NO: 56:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO: 56:

```
Gln Gly Trp Gly
1
```

(2) INFORMATION FOR SEQ ID NO: 57:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (xi) SEQUENCE DESCRIPTION: SEQ ID NO: 57:

```
Gln Val Ala Ala Arg Pro Gly
1               5
```

(2) INFORMATION FOR SEQ ID NO: 58:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO: 58:

```
Cys Ala Ser Ser
1
```

VACCINATION AND METHODS AGAINST MULTIPLE SCLEROSIS RESULTING FROM PATHOGENIC RESPONSES BY SPECIFIC T CELL POPULATIONS

This is a continuation-in-part of application Ser. No. 08/010,483, filed Jan. 28, 1993 now abandoned, which is a continuation of application Ser. No. 07/530,229, filed May 30, 1990, now abandoned, which is a continuation-in-part of application Ser. No. 07/382,085 and application Ser. No. 07/382,086, both filed Jul. 18, 1989 and both now abandoned, which are both continuation-in-parts of application Ser. No. 07/326,314, filed Mar. 21, 1989, now abandoned, the contents of which are incorporated by reference herein.

BACKGROUND OF THE INVENTION

This invention relates to the immune system and, more specifically, to methods of modifying pathological immune responses.

Higher organisms are characterized by an immune system which protects them against invasion by potentially deleterious substances or microorganisms. When a substance, termed an antigen, enters the body, and is recognized as foreign, the immune system mounts both an antibody-mediated response and a cell-mediated response. Cells of the immune system termed B lymphocytes, or B cells, produce antibodies which specifically recognize and bind to the foreign substance. Other lymphocytes termed T lymphocytes, or T cells, both effect and regulate the cell-mediated response resulting eventually in the elimination of the antigen.

A variety of T cells are involved in the cell-mediated response. Some induce particular B cell clones to proliferate and produce antibodies specific for the antigen. Others recognize and destroy cells presenting foreign antigens on their surfaces. Certain T cells regulate the response by either stimulating or suppressing other cells.

While the normal immune system is closely regulated, aberrations in immune response are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly effect such autoimmune pathologies.

Numerous diseases are believed to result from autoimmune mechanisms. Prominent among these are rheumatoid arthritis, systemic lupus erythematosus, multiple sclerosis, Type I diabetes, myasthenia gravis and pemphigus vulgaris. Autoimmune diseases affect millions of individuals worldwide and the cost of these diseases, in terms of actual treatment expenditures and lost productivity, is measured in billions of dollars annually. At present, there are no known effective treatments for such autoimmune pathologies. Usually, only the symptoms can be treated, while the disease continues to progress, often resulting in severe debilitation or death.

In other instances, lymphocytes replicate inappropriately and without control. Such replication results in a cancerous condition known as a lymphoma. Where the unregulated lymphocytes are of the T cell type, the tumors are termed T cell lymphomas. As with other malignancies, T cell lymphomas are difficult to treat effectively.

Thus there exists a long-felt need for an effective means of curing or ameliorating T cell mediated pathologies. Such a treatment should ideally control the inappropriate T cell response, rather than merely reducing the symptoms. The present invention satisfies this need and provides related advantages as well.

SUMMARY OF THE INVENTION

The present invention provides vaccines and a means of vaccinating a mammal so as to prevent or control specific T cell mediated pathologies or to treat the unregulated clonal replication of T cells. The vaccine is composed of a T cell receptor (TCR) or a fragment thereof corresponding to a TCR present on the surface of T cells mediating the pathology. The vaccine fragment can be a peptide corresponding to sequences of TCRs characteristic of the T cells mediating said pathology. The vaccine is administered to the mammal in a manner that induces an immunologically effective response so as to affect the course of the disease.

The invention additionally provides specific β-chain variable regions of the T cell receptor, designated Vβ6.2/3, Vβ6.5, Vβ2, Vβ5.1, Vβ13 and Vβ7, which are central to the pathogenesis of multiple sclerosis (MS). Also provided are means to detect, prevent and treat MS.

BRIEF DESCRIPTION OF THE FIGURES

FIG. 1 shows the frequency of the various TCR Vβ genes expressed in the cultures from CSF of MS patients.

FIG. 2 shows the sequences of the Vβ gene family that are most frequently expressed in the cultures from CSF of the MS patients.

FIG. 3 shows a summary of the Vβ7 CDR3 sequences. The top 3 monoclonal sequences were derived from cultured samples while the bottom sequences were obtained directly after sorting the CSF for CD25 (IL-2 receptor) and either CD3 or CD4.

DETAILED DESCRIPTION OF THE INVENTION

The invention relates to vaccines and their use for preventing or ameliorating T cell-mediated pathologies, such as autoimmune diseases and T cell lymphomas. Vaccination provides a specific and sustained treatment which avoids problems associated with other potential avenues of therapy.

As used herein, the term "T cell-mediated pathology" refers to any condition in which an inappropriate T cell response is a component of the pathology. The term is intended to include both diseases directly mediated by T cells and those, such as myasthenia gravis, which are characterized primarily by damage resulting from antibody binding, and also diseases in which an inappropriate T cell response contributes to the production of those antibodies. The term is intended to encompass both T cell mediated autoimmune diseases and unregulated clonal T cell replication.

As used herein, "substantially the amino acid sequence," or "substantially the sequence" when referring to an amino acid sequence, means the described sequence or other sequences having any additions, deletions or substitutions which do not substantially effect the ability of the sequence to elicit an immune response against the desired T cell receptor sequence. Such sequences commonly have many other sequences adjacent to the described sequence. A portion of the described immunizing sequence can be used so long as it is sufficiently characteristic of, the desired T cell receptor as to cause an effective immune response against desired T cell receptors but not against undesired T cell receptors. Such variations in the sequence can easily be made, e.g. by synthesizing an alternative sequence, and tested, e.g. by immunizing a mammal, to determine its effectiveness.

As used herein, the term "fragment" is intended to cover such fragments in conjunction with or combined with additional sequences or moieties, as for example where the peptide is coupled to other amino acid sequences or to a carrier. The terms "fragment" and "peptide" can, therefore, be used interchangeably since a peptide will be the most common fragment of the T cell receptor. Each fragment of the invention can have an altered sequence, as described above for the term "substantially the sequence."

As used herein, the term "vaccine" means compositions which, when administered into an individual, affect the course of the disease by causing an effect on the T cells mediating the pathology. This effect can include, for example, induction of cell mediated immunity or alteration of the response of the T cell to its antigen.

Reference herein to a "fragment or portion of the T cell receptor" does not mean that the composition must be derived from intact T cell receptors. Such "fragments or portions" can be produced by various means well-known to those skilled in the art, such as for example manual or automatic peptide synthesis or methods of cloning.

As used herein when referring to the relationship between peptide fragments of the invention and sequences of TCRs, "corresponding to" means that the peptide fragment has an amino acid sequence which is sufficiently homologous to the TCR sequence to stimulate an effective regulatory response in the individual. The sequence need not be identical to the TCR sequence, however, as shown in Examples II and III.

By "substantially pure" it is meant that the TCR or fragment thereof is substantially free of other biochemical moieties with which it is normally associated in nature. For example, the TCR is normally found with moieties derived from the same species of origin. Such moieties may act as undesirable contaminants when the TCR is used, for example, as a vaccine.

By "immunologically effective" is meant an amount of the T cell receptor or fragment thereof which, is effective to elicit a change in the immune response to prevent or treat a T cell mediated pathology or an unregulated T cell clonal replication in the individual. Obviously, such amounts will vary between species and individuals depending on many factors. For example, higher doses will generally be required for an effective immune response in a human compared with a mouse.

As used herein, "binding partner" means a compound which is reactive with a TCR. Generally, this compound will be a Major Histocompatibility Antigen (MHC) but can be any compound so long as when the TCR is bound in the normal course, T cell activation or proliferation occurs.

As used herein, "ligand" means any molecule that reacts to form a complex with another molecule.

As used herein, "selectively binds" means that a molecule binds to one type of molecule but not substantially to other types of molecules. In relation to Vβ17 "selective binding" indicates binding to Vβ17 containing TCRs but not substantially to other TCRs which lack Vβ17.

The immune system is the primary,biological defense of the host (self) against potentially pernicious agents (nonself). These pernicious agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

The principal manifestations of an antigen-specific immune response are humoral immunity (antibody mediated) and cellular immunity (cell mediated). Each of these immunological mechanisms are initiated through the activation of helper (CD4+) T Cells. These CD4+ T cells in turn stimulate B cells, primed for antibody synthesis by antigen binding, to proliferate and secrete antibody. This secreted antibody binds to the antigen and facilitates its destruction by other immune mechanisms. Similarly, CD4+ T cells provide stimulatory signals to cytotoxic (CD8+) T cells which recognize and destroy cellular targets (for example, virus infected cells of the host). Thus, the activation of CD4+ T cells is the proximal event in the stimulation of an immune response. Therefore, elaboration of the mechanisms underlying antigen specific activation of CD4+ T cells is crucial in any attempt to selectively modify immunological function.

T cells owe their antigen specificity to the T cell receptor (TCR) which is expressed on the cell surface. The TCR is a heterodimeric glycoprotein, composed of two polypeptide chains, each with a molecular weight of approximately 45 kD. Two forms of the TCR have been identified. One is composed of an alpha chain and a beta chain, while the second consists of a gamma chain and a delta chain. Each of these four TCR polypeptide chains is encoded by a distinct genetic locus containing multiple discontinuous gene segments. These include variable (V) region gene segments, junction (J) region gene segments and constant (C) region gene segments. Beta and delta chains contain an additional element termed the diversity (D) gene segment. (Since D segments and elements are found in only some of the TCR genetic loci, and polypeptides, further references herein to D segments and elements will be in parentheses to indicate the inclusion of these regions only in the appropriate TCR chains. Thus, V(D)J refers either to VDJ sequences of chains which have a D region or refers to VJ sequences of chains lacking D regions.)

During lymphocyte maturation, single V, (D) and J gene segments are rearranged to form a functional gene that determines the amino acid sequence of the TCR expressed by that cell. Since the pool of V, (D) and J genes which may be rearranged is multi-membered and since individual members of these pools may be rearranged in virtually any combination, the complete TCR repertoire is highly diverse and capable of specifically recognizing and binding the vast array of binding partners to which an organism may be exposed. However, a particular T cell will have only one TCR molecule and that TCR molecule, to a large degree if not singly, determines the specificity of that T cell for its binding partner.

Animal models have contributed significantly to our understanding of the immunological mechanisms of autoimmune disease. One such animal model, experimental allergic encephalomyelitis (EAE), is an autoimmune disease of the central nervous system that can be induced in mice and rats by immunization with myelin basic protein (MBP). The disease is characterized clinically by paralysis and mild wasting and histologically by a perivascular mononuclear cell infiltration of the central nervous system parenchyma. The disease pathogenesis is mediated by T cells with specificity for MBP. Multiple clones of MBP-specific T cells have been isolated from animals suffering from EAE and have been propagated in continuous culture. After in vitro stimulation with MBP, these T cell clones rapidly induce EAE when adoptively transferred to healthy hosts. Importantly, these EAE-inducing T cells are specific, not only for the same antigen (MBP), but also usually for a single epitope on that antigen. These observations indicate that discrete populations of autoaggressive T cells are responsible for the pathogenesis of EAE.

Analysis of the TCRs of EAE-inducing T cells has revealed restricted heterogeneity in the structure of these disease-associated receptors. In one analysis of 33 MBP-reactive T cells, only two alpha chain V region gene segments and a single alpha chain J region gene segment were utilized. Similar restriction of beta chain TCR gene usage was also observed in this T cell population. Only two beta chain V region segments and two J region gene segments were found. More importantly, approximately eighty percent of the T cell clones had identical amino acid sequences across the region of beta chain V-D-J joining. These findings confirm the notion of common TCR structure among T cells with similar antigen specificities and indicate that the TCR is an effective target for immunotherapeutic strategies aimed at eliminating the pathogenesis of EAE.

Various attempts have been made to exploit the antigen specificity of autoaggressive T cells in devising treatment strategies for EAE. For example, passive administration of monoclonal antibodies specific for TCRs present on EAE-inducing T cells has been employed. In the mouse model of EAE, infusion of a monoclonal antibody specific for $V_\beta 8$, the major beta chain V region gene used by MBP-specific T cells, reduced the susceptibility of mice to subsequent EAE induction (Acha-Orbea et al., Cell 54:263–273 (1988) and Urban et al., Cell 54:577–592 (1988)). Similar protection has been demonstrated in rat EAE with monoclonal antibody reactive with an unidentified idiotypic determinant of the TCR on MBP specific T cells (Burns et al., J. Exp. Med. 169:27–39 (1989)). While passive antibody therapy appears to have some ameliorative effect on EAE susceptibility, it is fraught with potential problems. The protection afforded is transient, thus requiring repeated administration of the antibody. Multiple infusions of antibody increases the chances that the host will mount an immune response to the administered antibody, particularly if it is raised in a xenogeneic animal. Further an antibody response to a pathogenic T cell clone represents only one element in the complete immune response and neglects the potential contributions of cellular immunity in resolving the autoreactivity.

The role of cellular immunity in reducing the activity of autoaggressive T cells in EAE has been examined and potential therapies suggested. In a manner similar to thee passive antibody approach, regulatory T cells have been derived ex vivo and readministered for immunotherapy. For example, Sun et al., Nature, 332:843–845 (1988), have recently isolated a CD8+ T cell line from convalescing rats in whom EAE had been induced by adoptive transfer of an MBP-specific CD4+ T cell line. This CD8+ T cell line displayed cytolytic activity in vitro for the CD4+ T cell used to induce disease. Moreover, adoptive transfer of this CTL line reduced the susceptibility of recipient rats to subsequent challenge with MBP. Lider et al., Science, 239:181–183 (1988) have also isolated CD8+ T cells with suppressive activity for EAE-inducing T cells. These CD8+ cells were isolated from rats vaccinated with attenuated disease-inducing T cell clones and, though they showed no cytolytic activity in vitro, they could suppress MBP-driven proliferation. of EAE-inducing T cells. Although these studies indicate that the CD8+ T cells could downregulate EAE, it is hard to reconcile a major role. for these selected CD8+ CTLs in the long-term resistance of the recovered rats since Sedgwick, et al., (Eur. J. Immunol., 18:495–502 (1988)) have clearly shown that depletion of. CD8+ cells with monoclonal antibodies does not affect the disease process or recovery.

In the experiments of Sun et al., and Lider et al., described above, the administration of extant derived regulatory T cells overcomes the major obstacle of passive antibody therapy; it permits a regulatory response in vivo of prolonged duration. However, it requires in vitro cultivation with attenuated disease-inducing T cells to develop clones of such regulatory T cells, a costly and labor intensive process. Further, in an outbred population such as humans, MHC non-identity among individuals makes this a highly individualized therapeutic strategy. Regulatory clones need to be derived for each individual patient and then re-administered only to that patient to avoid potential graft versus host reactions.

Direct vaccination with attenuated disease-inducing T cell clones also has been employed as a therapy for EAE. MBP-specific T cells, capable of transferring disease, have been attenuated by gamma irradiation or chemical fixation and used to vaccinate naive rats. In some cases, vaccinated animals exhibited resistance to subsequent attempts at EAE induction (Lider et al., supra; see Cohen and Weiner, Immunol. Today 9:332–335 (1988) for review). The effectiveness of such vaccination, however, is inconsistent and the degree of protection is highly variable. T cells contain a multitude of different antigens which induce an immune response when the whole T cell is administered as a vaccine. This phenomenon has been demonstrated by Offner et al., (J. Neuroimmunol., 21:13–22 (1989)), who showed that immunization with whole T cells increased the delayed type hypersensitivity (DTH) response, as measured by ear swelling, to those T cells in an incremental manner as the number of vaccinations increased. However, positive DTH responses were found in both protected and non-protected animals. Rats responded similarly to both the vaccinating encephalitogenic T cells and control T cells.

Conversely, vaccination with PPD-specific T cells from a PPD-specific T cell line induced DTH to the vaccinating cells as well as to an encephalitogenic clone even though no protection was observed. The similar response of vaccinated rats to both disease-inducing and control cells, as quantified by delayed-type hypersensitivity (a measure of cell-mediated immunity), indicates that numerous antigens on these T cells are inducing immune responses. Thus, vaccination with attenuated disease-inducing T cells suffers from a lack of specificity, for the protective antigen on the surface of that T cell, as well as, variable induction of immunity to that antigen. As a candidate for the treatment of human diseases, vaccination with attenuated T cells is plagued by the same labor intensiveness and need for individualized therapies as noted above for infusion of CD8+ cells.

The present invention provides an effective method of immunotherapy for T cell mediated pathologies, including autoimmune diseases such as multiple sclerosis, which avoids many of the problems associated with the previously suggested methods of treatment. By vaccinating, rather than passively administering heterologous antibodies, the host's own immune system is mobilized to suppress the autoaggressive T cells. Thus, the suppression is persistent and may involve any and all immunological mechanisms in effecting that suppression. This multi-faceted response is more effective than the uni-dimensional suppression achieved by passive administration of monoclonal antibodies or extant-derived regulatory T cell clones.

As they relate to autoimmune disease, the vaccines of the present invention comprise TCRs of T cells that mediate autoimmune diseases. The vaccines can be whole TCRs substantially purified from T cell clones, individual T cell receptor chains (for example, alpha, beta, etc.) or portions of such chains, either alone or in combination. The vaccine can be homogenous, for example, a single peptide, or can be composed of more than one type of peptide, each of which corresponds to a different portion of the TCR. Further, these peptides can be from distinct TCRs wherein both TCRs contribute to the T cell mediated pathology.

The Vβ6 TCR subunits were sequenced from 8 patients. From these 8 patients three-quarters (6 of 8) were identified as members of the Vβ6.2/3 and Vβ6.5 subfamily shown in FIG. 2. These two subfamilies of the Vβ6 gene family show considerable homology in the CDR2 region between residues 39 and 58. It appears that these two particular members of the Vβ6 family are particularly associated with multiple sclerosis.

In a further specific embodiment, T cell receptors, whole T cells or fragments of the TCR which contain the Vβ chains designated Vβ6.2/3, Vβ6.5, Vβ2, Vβ5.1, Vβ13, Vβ7 can be used to immunize an individual having or at risk of having multiple sclerosis to treat or prevent the disease. The immune response generated in the individual can neutralize or kill T cells having the particular Vβ subunit and, thus, prevent or treat the deleterious effects of the Vβ-bearing T cells. Moreover, to the extent that these Vβ subunits are common to T cell receptors on pathogenic T cells mediating autoimmune diseases in general, such vaccines can also be effective in ameliorating such other autoimmune diseases.

The vaccines comprise peptides, of varying lengths corresponding to the TCR or portions thereof. The peptides can be produced synthetically or recombinantly, by means well known to those skilled in the art. Preferably, the peptide vaccines correspond to regions of the TCR which distinguish that TCR from other nonpathogenic TCRs. Such specific regions can be located within the various region(s) of the respective TCR polypeptide chains, or spanning the various regions such as a short sequence spanning the V(D)J junction, thus restricting the immune response solely to those T cells bearing this single determinant.

The vaccines are administered to a host exhibiting or at risk of exhibiting an autoimmune response. Definite clinical diagnosis of a particular autoimmune disease warrants the administration of the relevant disease-specific TCR vaccines. Prophylactic applications are warranted in diseases where the autoimmune mechanisms precede the onset of overt clinical disease. Thus, individuals with familial history of disease and predicted to be at risk by reliable prognostic indicators could be treated prophylactically to interdict autoimmune mechanisms prior to their onset.

TCR vaccines can be administered in many possible formulations, in pharmacologically acceptable mediums. In the case of a short peptide, the peptide can be conjugated to a carrier, such as KLH, in order to increase its immunogenicity. The vaccine can be administered in conjunction with an adjuvant, various of which are known to those skilled in the art. After initial immunization with the vaccine, a booster can be provided. The vaccines are administered by conventional methods, in dosages which are sufficient to elicit an immunological response, which can be easily determined by those skilled in the art.

Appropriate peptides to be used for immunization can be determined as follows. Disease-inducing T cell clones reactive with the target antigens are isolated from affected individuals. Such T cells are obtained preferably from the site of active autoaggressive activity such as a lesion in the case of pemphigus vulgaris, central nervous system (CNS) in the case of multiple sclerosis or synovial fluid or tissue in the case of rheumatoid arthritis, or alternatively from blood of affected individuals. The TCR genes from these autoaggressive T cells are then sequenced. Polypeptides corresponding to TCRs or portions thereof that are selectively represented among disease inducing T cells (relative to non-pathogenic T cells) can then be selected as vaccines and made and used as described above.

Alternatively, the vaccines can comprise anti-idiotypic antibodies which are internal images of the peptides described above. Methods of making, selecting and administering such anti-idiotype vaccines are well known in the art. See, for example, Eichmann, et al., CRC Critical Reviews in Immunology 7:193–227 (1987), which is incorporated herein by reference.

Multiple Sclerosis

T cells causative of multiple sclerosis (MS) have not previously been identified, though MBP-reactive T cells have been proposed to play a role due to the clinical and histologic similarities between MS and EAE. In rat and mouse models of EAE, MBP-reactive, encephalogenic T cells show striking conservation of β-chain VDJ amino acid sequence, despite known differences in MHC restriction and MBP-peptide antigen specificity. This invention is premised on the observation that a human myelin basic protein (MBP)-reactive T cell line, derived from an MS patient, has a TCR β-chain with a VDJ amino acid sequence homologous with that of β-chains from MBP-reactive T cells mediating pathogenesis in experimental allergic encephalomyelitis (EAE), an animal model of MS. This line is specific for another epitope of MBP. This finding demonstrates the involvement of MBP-reactive T cells in the pathogenesis of MS and demonstrates that TCR peptides similar to those described herein for the prevention of EAE can be appropriate in treating MS.

Specifically, the invention provides a method of diagnosing or predicting susceptibility to T cell mediated pathologies in an individual comprising detecting T cells having the β-chain variable regions designated Vβ6.2/3, Vβ6.5, Vβ5.1, Vβ7, Vβ13, or Vβ2 in a sample from the individual, the presence of abnormal levels of these Vβ-containing T cells indicating the pathology or susceptibility to the pathology. The Vβ containing T cell can be qualitatively or quantitatively compared to that of normal individuals. Such diagnosis can be performed for example by detecting a portion of the Vβ which does not occur on multiple sclerosis associated β-chain variable region T-cell receptors. The Vβ can be detected, for example, by contacting the Vβ with a detectable ligand capable of specifically binding to Vβ. Many such detectable ligands are known in the art, e.g. an enzyme linked antibody. Alternatively, nucleotide probes complementary to the Vβ subunit-encoding nucleic acid sequences can be utilized to detect T cells containing the corresponding Vβ subunit, as taught in Examples VIII and IX.

The invention also provides a method of preventing or treating a T cell mediated pathology comprising preventing the attachment of the Vβ subunit containing T-cell receptor to its binding partner. In one embodiment attachment is prevented by binding a ligand to the Vβ subunit. In an alternative embodiment attachment is prevented by binding a ligand to the binding partner. Attachment can be prevented by known methods, e.g. binding an antibody to the subunit or the binding partner to physically block attachment.

The invention also provides a method of preventing or treating a T cell mediated pathology in an individual comprising cytotoxicly or cytostaticly treating T-cells containing the particular Vβ subunit in the individual. In one embodiment, the Vβ containing T-cells are treated with a cytotoxic or cytostatic agent which selectively binds the Vβ. The agent can be an antibody attached to a radioactive or chemotherapeutic moiety. Such attachment and effective agents are well known in the art. See, for example, Harlow, E. and Lane, Antibodies, A Laboratory Manual, Cold Spring Harbor Laboratory, 1988, which is incorporated herein by reference.

The invention also provides a method of preventing or treating multiple sclerosis in an individual comprising cytotoxicly or cytostaticly treating cells containing substantially the SGDQGGNE (SEQ ID NO:1) sequence in the individual. In one embodiment, T-cells are treated with a cytotoxic or cytostatic agent which selectively binds the sequence. The agent can be an antibody attached to a radioactive or chemotherapeutic moiety.

The following examples are intended to illustrate but not limit the invention.

EXAMPLE I

Rat Model of EAE

Female Lewis rats, (Charles River Laboratories, Raleigh-Durham, N.C.) were immunized in each hind foot pad with 50 μg of guinea pig myelin basic protein emulsified in complete Freund's adjuvant. The first signs of disease were typically observed 9–11 days post-immunization. Disease severity is scored on a three point scale as follows: 1=limp tail; 2=hind leg weakness; 3=hind leg paralysis. Following a disease course of approximately four to six days, most rats spontaneously recovered and were refractory to subsequent EAE induction.

EXAMPLE II

Selection and Preparation of Vaccines

Vaccinations were conducted with a T cell receptor peptide whose sequence was deduced from the DNA sequence of a T cell receptor beta gene predominating among EAE-inducing T cells of B10.PL mice. The DNA sequence was that reported by Urban, et al., supra, which is incorporated herein by reference. A nine amino acid peptide, having the sequence of the VDJ junction of the TCR beta chain of the mouse, was synthesized by methods known to those skilled in the art. The sequence of this peptide is: SGDAGGGYE (SEQ ID NO:2. (Amino acids are represented by the conventional single letter codes.) The equivalent sequence in the rat has been reported to be: SSD-SSNTE (SEQ ID NO:3) (Burns et al., J. Exp. Med. 169:27–39 (1989)). The peptide was desalted by Sephadex G-25 (Pharmacia Fine Chemicals, Piscataway, N.J.) column chromatography in 0.1 M acetic acid: and the solvent was subsequently removed by two cycles of lyophilization. A portion of the peptide was conjugated to keyhole limpet hemocyanin (KLH) with glutaraldehyde at a ratio of 7.5 mgs of peptide per mg of KLH. The resulting conjugate was dialyzed against phosphate buffered saline (PBS).

EXAMPLE III

Vaccination Against EAE

Vaccines used in these studies consisted of free VDJ peptide and also of VDJ peptide conjugated to KLH. These were dissolved in PBS and were emulsified with equal volumes of either (1) incomplete Freund's adjuvant (IFA) or (2) complete Freund's adjuvant (CFA) made by suspending 10 mg/ml heat killed desiccated *Mycobacterium tuberculosis* H37ra (Difco Laboratories, Detroit, Mich.) in IFA. Emulsions were administered to 8–12 week old female Lewis rats in a final volume of 100 microliters per animal (50 μl in each of the hind footpads). 5 μg of unconjugated VDJ peptide were administered per rat. KLH-VDJ conjugate was administered at a dose equivalent to 10 μg of KLH per rat. Twenty-nine days later each rat was challenged with 50 μg of guinea pig myelin basic protein in complete Freund's adjuvant in the front footpads. Animals were monitored daily beginning at day 9 for clinical, signs of EAE and were scored as described above. The results are presented in Table I. As can be seen, not only was there a reduced incidence of the disease in the vaccinated individuals, but in those which did contract the disease, the severity of the disease was reduced and/or the onset was delayed. The extent of protection varied with the vaccine formulation, those including CFA as the adjuvant demonstrating the greatest degree of protection.

TABLE I

| Animal No. | Vaccination (Adjuvant) | Days After Challenge | | | | | | | | |
|---|---|---|---|---|---|---|---|---|---|---|
| | | 10 | 11 | 12 | 13 | 14 | 15 | 16 | 17 | 18 |
| 1 | VDJ (IFA) | — | — | 2 | 3 | 3 | 3 | — | — | — |
| 2 | " | — | — | 1 | 3 | 3 | 3 | 2 | — | — |
| 3 | " | — | — | — | 3 | 3 | 3 | 2 | — | — |
| 4 | VDJ (CFA) | — | — | — | — | 1 | 1 | 1 | — | — |
| 5 | " | — | — | — | — | — | — | — | — | — |
| 6 | " | — | — | — | 1 | 3 | 3 | 3 | 2 | — |
| 7 | KLH-VDJ (CFA) | — | — | — | 1 | 3 | 2 | — | — | — |
| 8 | " | — | — | — | — | 1 | 1 | 1 | 1 | — |
| 9 | " | — | — | — | — | — | — | — | — | — |
| 10 | KLH-VDJ (IFA) | — | 1 | 3 | 3 | 2 | 2 | 1 | — | — |
| 11 | " | — | — | 3 | 3 | 3 | 3 | 3 | 2 | — |
| 12 | " | — | — | 1 | 3 | 3 | 3 | 3 | — | — |
| 13 | NONE | 1 | 3 | 3 | 3 | 3 | 1 | — | — | — |
| 14 | " | — | 1 | 3 | 3 | 3 | 1 | — | — | — |
| 15 | " | 1 | 3 | 3 | 3 | 1 | — | — | — | — |

Scoring:
— no signs
1) limp tail
2) hind leg weakness
3) hind leg paralysis

EXAMPLE IV

Vaccination against EAE with Lewis Rat VDJ Peptides

The VDJ peptide used in the previous examples was synthesized according to the sequence of TCR β chain molecules found on EAE-inducing T cells in B10.PL mice. In addition, peptides were synthesized and tested which correspond to sequences found on encephalitogenic T cells in Lewis rats. These VDJ sequences are homologous with that of B10.PL mice, but not identical. The rat peptides were synthesized according to the DNA. sequences reported by Burns, et al. and Chluba, et al., Eur. J. Immunol. 19:279–284 (1989). The sequences of these peptides designated IR1, 2, 3 and 9b are shown below, aligned with the B10.PL mouse sequence used in Examples I through III (VDJ).

```
VDJ         S G D A G G Y E
            (SEQ ID NO: 4)

IR1         C A S S D - S S N T E V F F G K
            (SEQ ID NO: 5)

IR2         C A S S D - S G N T E V F F G K
            (SEQ ID NO: 6)

IR3         C A S S D - S G N - V L Y F G E G S R
            (SEQ ID NO: 7)

IR9b        A S S D - S S N T E
            (SEQ ID NO: 8)
```

The preparation, administration and evaluation of these vaccines were conducted as described in Examples I through III with the following exceptions: 50 μg of the individual VDJ peptides were incorporated into vaccine formulations containing CFA; neither vaccinations in IFA nor vaccinations with peptides conjugated to KLH were conducted. Control animals were untreated prior to MBP challenge as in Example III or were vaccinated with emulsions of PBS and CFA to assess the protective effect of adjuvant alone. The results are shown in Table II below.

TABLE II

| Animal No. | Vaccination (Adjuvant) | Days After Challenge | | | | | | | |
|---|---|---|---|---|---|---|---|---|---|
| | | 10 | 11 | 12 | 13 | 14 | 15 | 16 | 17 | 18 |
| 1 | None | — | 1 | 2 | 3 | 3 | 2 | — | — | — |
| 2 | " | 1 | 3 | 3 | 3 | 2 | — | — | — | — |
| 3 | " | — | 2 | 3 | 3 | 3 | 1 | — | — | — |
| 4 | PBS-CFA | 1 | 2 | 3 | 3 | 3 | — | — | — | — |
| 5 | " | 1 | 2 | 3 | 3 | 3 | — | — | — | — |
| 6 | " | — | 2 | 3 | 3 | 3 | — | — | — | — |
| 7 | IR1 (50 μg) | — | — | — | 2 | 1 | — | — | — | — |
| 8 | " | — | — | — | — | 1 | 3 | — | — | — |
| 9 | " | — | — | — | 1 | 1 | 1 | 1 | — | — |
| 10 | IR2 (50 μg) | — | — | 1 | 3 | 3 | 3 | — | — | — |
| 11 | " | — | — | — | — | 2 | 2 | 3 | 3 | — |
| 12 | " | — | — | — | — | 1 | — | — | — | — |
| 13 | IR3 (50 μg) | 1 | 3 | 3 | 3 | 2 | — | — | — | — |
| 14 | " | — | — | 2 | 3 | 3 | — | — | — | — |
| 15 | " | — | — | — | — | — | — | — | — | — |
| 16 | IR9b (50 μg) | — | — | — | — | — | — | — | — | — |
| 17 | " | — | — | — | — | — | — | — | — | — |
| 18 | " | — | — | — | — | — | — | — | — | — |
| 19 | " | — | — | — | — | — | — | — | — | — |

Scoring:
— no signs
1) limp tail
2) hind leg weakness
3) hind leg paralysis

As shown in Table II, disease in unvaccinated control animals was observed as early as day 10. Disease was characterized by severe paralysis and wasting, persisted for 4 to 6 days and spontaneously remitted. PBS-CFA vaccinated rats displayed disease courses virtually indistinguishable from those of unvaccinated controls. In contrast, delays in onset were observed in some of the IR1, 2 or 3 vaccinated animals and others showed both delayed onset as well as decreased severity and/or duration of disease. Overall, however, vaccinations with the rat VDJ peptides (IR1–3) were slightly less effective than those with the mouse VDJ peptide (Example III). Vaccination with IR9b, however, afforded complete protection in all four animals in which it was tested. Importantly, no histologic lesions characteristic of disease were found in any of the four animals vaccinated with IR9b indicating that sub-clinical signs of disease were also abrogated.

EXAMPLE V

Vaccination with V Region Specific Peptides

A peptide specific for the Vβ8 gene family was tested as a vaccine against EAE. Vβ8 is the most common β chain gene family used by encephalitogenic T cells in both rats and mice. A peptide was synthesized based on a unique DNA sequence found in the Vβ8 gene, and which is not found among other rat Vβ genes whose sequences were reported by Morris, et al., Immunogenetics 27:174–179 (1988). The sequence of this Vβ8 peptide, designated IR7, is:

IR7 DMGHGLRLIHYSYDVNSTEK(SEQ ID NO:9)

The efficacy of this Vβ8 peptide was tested in the Lewis rat model of EAE (Example I) as described in Examples II and III. 50 μg of peptide were tested in CFA. Vaccinations in IFA or with peptide-KLH conjugates were not conducted. The results of these studies are shown in Table III.

TABLE III

| Animal No. | Vaccination (Adjuvant) | Days After Challenge | | | | | | | | |
|---|---|---|---|---|---|---|---|---|---|---|
| | | 10 | 11 | 12 | 13 | 14 | 15 | 16 | 17 | 18 |
| 1 | IR7 (50 μg) | — | — | 1 | 2 | 3 | 3 | 3 | — | — |
| 2 | " | — | — | — | — | 1 | 1 | — | — | — |
| 3 | " | — | — | — | — | — | — | — | — | — |

Scoring:
— no signs
1) limp tail
2) hind leg weakness
3) hind leg paralysis

The results of vaccinations conducted with the rat Vβ8 peptide are similar to those observed with the mouse and rat IR1, 2 and 3 peptides. Delayed onset as well as decreased severity and duration of disease was observed in one animal. One animal was completely protected.

EXAMPLE VI

Vaccination with J Region Peptides

A peptide was synthesized which corresponds to the J α gene segment, TA39, found among; both rat and mouse encephalitogenic T cell receptors. The sequence of this peptide, designated IR5, is:

IR5 RFGAGTRLTVK(SEQ ID NO:10)

The efficacy of the JαTA39 peptide was tested in the Lewis rat model of EAE (Example I) as described in Examples II and III. 50 μg of peptide were tested in CFA. Vaccinations in IFA or with peptide-KLH conjugates were not conducted. The results of these studies are shown in Table IV.

TABLE IV

| Animal No. | Vaccination (Adjuvant) | Days After Challenge | | | | | | | | | |
|---|---|---|---|---|---|---|---|---|---|---|---|
| | | 10 | 11 | 12 | 13 | 14 | 15 | 16 | 17 | 18 | 19 | 20 |
| 1 | IR5 (50 μg) | — | — | — | — | — | — | 2 | 1 | 1 | 1 | 1 | — |
| 2 | " | — | — | — | — | — | — | — | — | — | — | — | — |
| 3 | " | — | — | — | — | — | — | — | — | — | — | — | — |

Scoring:
— no signs
1) limp tail
2) hind leg weakness
3) hind leg paralysis

The results of vaccinations conducted with the rat J α TA39 peptide are more effective than those observed with the mouse VDJ peptide or the Vβ8 peptide. Two of three animals were totally protected and, in the third, disease onset was markedly delayed. Severity was also reduced in this animal though disease persisted for a normal course of 5 days. Importantly, the two animals which were completely protected showed no histologic evidence of T cell infiltration of the CNS. This result indicates that vaccinating with the $J_\alpha TA39$ very, efficiently induces a regulatory response directed at encephalitogenic T cells. Even sub-clinical signs of disease were abrogated.

EXAMPLE VII

Vaccination with Mixtures of TCR Peptides

Vaccinations were conducted with a mixture of TCR peptides. This mixture contained 50 μg of each of the peptides IR1, 2, 3 and 5 (the three rat VDJ peptides and the rat JαTA39 peptide).

The efficacy of this peptide mixture was tested in the Lewis rat model (Example I) as described in Examples II and III. Peptides were tested in CFA. Vaccinations in IFA or with peptide-KLH conjugates were not conducted. The results of these studies are shown in Table V.

TABLE V

| Animal No. | Vaccination (Adjuvant) | Days After Challenge |||||||||
|---|---|---|---|---|---|---|---|---|---|---|
| | | 10 | 11 | 12 | 13 | 14 | 15 | 16 | 17 | 18 |
| 4 | IR1, 2, 3, 5 | — | — | — | — | — | — | — | — | — |
| 5 | (50 μg each) | — | — | — | — | — | — | — | — | — |
| 6 | " | — | — | — | — | — | — | — | — | — |

Scoring:
— no signs
1) limp tail
2) hind leg weakness
3) hind leg paralysis

The results of vaccinations conducted with the rat JαTA39 and three VDJ peptides were as effective as those described for IR9b in Table II. All three animals were totally protected. In addition to the absence of any clinical signs of EAE, two of these three animals were completely free of histological evidence of T cell infiltration into the CNS while the third showed only two small foci of lymphocytic infiltration at the base of the spinal cord.

EXAMPLE VIII

Multiple Sclerosis Vaccine

CSF Cells: Cerebrospinal fluid (CSF) was obtained from 28 patients who were tapped at least once. Twelve were tapped twice and one tapped three times. In addition three pateient's CSF cells were cultured and assessed in duplicate. Fifty-150 thousand lymphocytes were recovered from 20 ml CSF; these cells were spun down and resuspended in 200 μl human T cell media (HTC) which consists of RPMI 1640 supplemented with human AB serum (15%), glutamine (2 mM), HEPES buffer (10 mM), 2-mercaptoethanol (0.05 mM), and the antibiotics penicillin and streptomycin (each 5 iu/ml). A small aliquot (20 thousand cells) was set aside for flow cytometric analysis following staining with monoclonal antibodies Mabs specific for CD25 (IL-1R), CD4 and CD8, and irrelevant (control antibodies) directly coupled to fluorescein isothiocyanate (FITC) and phycoerythrin (PE).

The remaining cells (30–130 thousand) were exposed to washed DYNABEADS (Dynal Inc., Great Neck, N.Y.) (ratio 1:20) coupled with Mab specific for human CDBα chains. CD8$^+$ T cells coupled to these beads stick to the walls of the tube in a magnetic field and CD8$^-$ T cells were recovered by pipetting off the fluid. Generally, this provides a yield of 70–80% (20–100 thousand cells) with greater than 95% depletion of cells bearing the CD8 marker.

The remaining cell population consists, at this point mostly of CD4$^+$ T cells, half or more of which are activated and express the CD25 marker (IL-2R). These activated T cells were expanded in cultures (20–50 thousand cells per well) of HTC medium supplemented with 20% Lymphocult-T-LF (Biotest Diagnostics Corp.; Denville, N.J.) and with recombinant human IL-2 and IL-4 (R & D Systems, Minneapolis, Minn.) (50 μ/ml). Cultures were fed twice weekly; generally, after 1 week, cells began to overgrow their cultures. Each well was split into three, and four days later into six, wells. After 10 days to 2 weeks of culture, the initial inoculum generated more than 1 million cells. Flow cytometric analysis of the cultured cells indicated more than 95% were CD4$^+$CD8$^-$CD3$^+$TCRαβ$^{30}$. Occasionally a majority of cells. were CD4$^-$CD8$^-$CD3$^+$, a population assumed to be rich in TCRγδ$^+$ T cells.

Total cellular RNA was isolated from T cell populations following lysis in guanidinium isothiocyanate and phenol extraction (Chomczynski, P., and N. Sacchi,. "Single-Step Method of RNA Isolation by Acid Guanidinium Thiocyanate-Phenol-Chloroform Extraction," *Analy. Biochem.* 162:156 (1987), which is incorporated herein by reference. The RNA (3–5 μg) was first denatured in methyl mercuric hydroxide (10 mM final concentration; Alfa Products, Ward Hill, Mass.) and then converted to cDNA in Taq (*Thermus aquaticus*) DNA polymerase buffer (Perkins Elmer Cetus; Norwalk, Conn.) (50 mM KCl, 10 mM Tris-HCl pH8.3, 2.5 mM MgCl$_2$, and 0.01% gelatin) in the presence of RNasin (20 units, Promega, Madison, Wis.), β-mercaptoethanol (40 mM), dNTPs (0.5 mM, Pharmacia), Cβ specific oligonucleotide primer (Cβ-1; 1 μM) and AMV (Avian myeloblastosis virus) reverse transcriptase (8 units, U.S. Biochemical, Cleveland, Ohio) in a 25 μl reaction for 90 minutes at 42° C. The Cβ oligonucleotide primer, (Cβ-1), is complementary to a sequence found at the C terminal of human Cβ1 and Cβ2 mRNA.

PCR amplification: cDNA was transferred to a tube containing the following: a Cβ-2 primer (0.6 μM) corresponding to a sequence more internal to Cβ-1 used in cDNA synthesis, dNTPs (200 μM) and Taq DNA polymerase (23u, Perkin Elmer Cetus, Norwalk, Conn.), in Taq polymerase buffer as above except for the presence of 1.5 mM MgCl$_2$. Fifty μl of this mixture is added to each of 30 individual wells of a microtest III U bottom flexible assay plate (Falcon, 3911; Becton Dickinson and Co., Oxnard, Calif.). Each well contained a different oligonucleotide Vβ primer specific for one of the 30 known human Vβ families shown in the accompanying table (0.6 μM in 1 μl) or no Vβ primer as control. The wells were overlain with light mineral oil (Sigma; St. Louis, Mo.), heated to 94° C. for 5 minutes to denature DNA/RNA duplexes and then subjected to 27 amplification cycles of 1 minute at 94° C. for melting, 1.5 minutes at 55° C. for annealing, and 2 minutes at 72° C. for extension in a 96 well thermal cycler (MJ Research,Inc.; Watertown, Mass.).

Quantitation of Vβ expression: Following amplification, 15 μl of the PCR product was denatured for 20 minutes at room temperature by the addition of 15 μl 1N NaOH. The samples were then neutralized by the addition of 15 μl 1N HCl and 15 μl 20×SSC. 15 μl of the neutralized samples was spotted onto nitrocellulose filters (BA85, Schleicher &

Schuell; Keene, N.H.) using a Bio-Dot microfiltration apparatus (Bio-Rad Laboratories; Richmond, Calif.) and then cross-linked to the filter using a UV Stratalinker 1800 according to manufacturer's recommendations (Stratagene; San. Diego, Calif.). The relative 10-level of amplification in each well was assessed by probing with a gamma $^{32}$p (DuPont; Boston, Mass.) end-labelled Cβ specific oligonucleotide, Cβ-3, which was further 5' to the Cβ oligonucleotide used in the PCR. Filters were pre-hybridized at 37° C. for 1–2 hours in a. mixture containing 6×SSC, 1×Denhardt's solution, 0.5% SDS, 0.05% sodium pyrophosphate, and 100 μg/ml sonicated salmon sperm DNA (Salmon sperm DNA Cat.#1626; Sigma; St. Louis, Mo.). The filters were then hybridized with the radiolabeled oligonucleotide Cβ primer overnight at 37° C. in a mixture containing 6×SSC, 1×Denhardt's, 0.1% SDS, 0.05% sodium pyrophosphate and 20 μg/ml wheat germ tRNA (Type V, Sigma; St. Louis, Mo.). Following hybridization, the filters were washed twice at 37° C. for 30 minutes in 6×SSC containing 0.05% sodium pyrophosphate and one time more at 47° C. for 10 minutes. The level of hybridization for each Vβ was measured using an AMBIS radioisotope detector (Ambis; San Diego, Calif.). All values are corrected by subtracting counts incorporated into the water blank control well. Relative Vβ expression was calculated by summing all counts detected and dividing this value into the net counts for any given well.

A summary of results of TCR β chain usage among T cells in the CSF of MS patients is presented in FIG. 1. As can be seen, Vβ2 was expressed on greater than 70% of the cultured CSF T cells from 1 patient, 50–59% of T cells from another, 20–29% from 4 others, and so forth.

Assuming 30–50 different Vβ members in the repertoire of human T cell receptors, each being represented randomly, the frequency of any one TCR Vβ member would be expected to be approximately 2–3% of the total in a given T cell population. In fact, one rarely finds expression of any particular Vβ chain exceeding 10% in the peripheral blood T cell pool of a normal individual. FIG. 1 indicates the disproportionate usage (greater than 20%) of at least 4 different Vβ members among the T cells of CSF from MS patients.

In order of most frequent usage (greater than 20%) Vβ6.2/3 or Vβ6.5 are used disproportionately in 13 samples, Vβ2 in 6 samples, Vβ5.1 and Vβ13 in 4 samples each. Thus, among 39 samples, 27 of them show a disproportionate usage of one or more of these 4 different TCR Vβ members.

The predicted amino acid sequences of these Vβ members is shown in FIG. 2.

Based on preliminary data gathered over the past year, a peptide of the CDR2 region of Vβ6.5 encompassing amino acids 39–58 was made 39-LeuGlyGlnGlyProGluPheLeuThr TyrPheGlnAsnGluAlaGlnLeuGluLys Ser-58. (LGQGPEFLTYFQNEAQLEKS) (SEQ ID NO:11) This region is nearly identical to the corresponding sequences found in Vβ6.2/3, Vβ6.8 and Vβ6.9, and differs only slightly from sequences found in Vβ6.4, Vβ6.7, and Vβ6w1. This peptide is effective in provoking an immune response against TCR of most of the Vβ6 family.

Of the 13 samples (from 12 patients) where Vβ6.2/3 or Vβ6.5 was used heavily, sequence studies have been conducted on material from 8 patients to determine (i) the degree of clonality based on homogeneity of sequences in the CDR3 junctional region and (ii) which of the many members of the Vβ6.2/3 and Vβ6.5 family is involved.

DNA Sequencing. To determine the DNA sequence of the expressed Vβ, the PCR reaction was repeated as described above for 30 cycles with Cβ-1 and the Vβ6 specific primer. Following amplification, the resulting PCR products were first made blunt-ended by addition of 5 units T4 DNA polymerase (Pharmacia Fine Chemicals; Piscataway, N.J.) for 15 minutes at 37° C., then extracted with chloroform to remove mineral oil, precipitated with ethanol, and digested with EcoR1 according to manufacturer's specifications (New England Biolabs; Beverley, Mass.); the resulting DNA was separated on a 1.4% agarose gel (Ultra PURE Agarose, GIBCO BRL; Gaithersburg, Md.). The appropriate size product was Isolated using Prep-A-Gene (Bio-Rad; Richmond, Calif.), ligated into the Hincll/EcoR1 site of pBluescript II (Stratagene; San Diego, Calif.), and the ligation mixture was then transformed into the bacterial strain DH5 (available from GIBCO, BRL). Multiple ampicillin resistant colonies were selected and miniprep DNA was prepared by standard methods (Maniatas, T., E. F. Fritsch, and J. Sambrook. 1982. Molecular cloning, a laboratory manual. Cold Spring Harbor Laboratory, New York which is incorporated herein by reference). The plasmid DNA was then sequenced directly by dideoxy chain termination (Sanger, F., S. Nicklen, and A. R. Coulson, "DNA sequencing with chain-terminating inhibitors." *Proc. Natl. Acad. Sci. USA*. 78:5453 (1977), which is incorporated herein by reference, using the Sequenase sequencing method (U.S. Biochemical, Cleveland, Ohio).

These studies established that Vβ utilization is indeed clonal, displaying shared CDR3 sequences on a majority of the PCR amplified material, and that a single Vβ6.2/3 and Vβ6.5 family member dominates. To date, of the 8 patients, 4 use Vβ6.5, 1 uses Vβ6.4, 2 use Vβ6.2, and 1 uses Vβ36.1. These results indicate that the peptide vaccine would be effective for 6 or 7 of the 8 patients.

EXAMPLE IX

A study was performed on CSF samples from MS patients in which Vβ7 was a dominant clone in 3 out of a total of 5 samples. The protocol used was parallel to that provided in Example VIII with the following. modifications. The oligonucleotide primers have different amplification efficiencies and can amplify additional TCR Vβ subfamily members than those described above. In addition, the CSF samples were not depleted of CD8+ cells.

Unfractionated CSF were cultured in single or duplicate microtiter wells for 14–23 days in IL-2/IL-4 and Lymphocult (Biotest Diagnostics Corp.; Denville, N.J.) (hereafter referred to as the "culture") as described above. The T cell subset phenotyping was performed after this culture period and is summarized in Table XI as the percentage each of CD4+ and CDB+ T cells. For patients 88 and 94, the CSF samples were split into 2 wells prior to culturing which is noted as well 1 and well 2. It is clear from this that in nearly all CSF and PBL samples, over 50% of the cultured cells were CD4+, which is desirable since it is this population which is of most interest.

In patient 82 a TCR usage was dominated by Vβ7 and 18, which account for approximately 65% of the total signal (as assessed by Ambis scanning). This dominant or "restricted" Vβ usage was. explored further by sequencing the CDR3 domain, the most variable region of the TCR β chain and one believed to be important in binding antigen. Table XIII shows that the dominant Vβ7 of the PCR arose from one cell as assessed by the monoclonal (11/11 clones sequenced were identical) CDR3 domain. Vβ18 was oligoclonal in that 2 cells contributed to the PCR product as seen by 2 discrete CDR3 domains.

Surprisingly, when the material from patient 88 was equally split into 2 wells and treated identically, different dominant clones arose. Well 1 was dominated by Vβ14 while well 2 had dominant Vβ7 and 20. Table 4 reveals the CDR3 domains of several of the clones growing in each well and indicates that each was clonal. Restricted Vβ usage in the cultured CSF samples was not true for the patient's PBLs cultured at similar densities (FIG. 3). The Vβ profile for the PBLs were more diverse, where more of the signal was contributed by a wider variety of T cells.

The CSF sample from patient 94 was again split into 2 replicate samples prior to culture. Like the previous samples, there is evidence of a restricted Vβ usage by clones expanded by the culture conditions. Both populations were over 75% CD4+ (Table 2). However, like CSF 88, there were different dominant clones growing in each well although Vβ3 was dominant in both wells. Table 5 reveals that while the CDR3 domains of Vβ3 for each clone are monoclonal, they are discrete rearrangements, indicating that they did not descend from one progenitor. This observation is presently being investigated.

The cultured CSF and PBLs from patient 95 contained a dominant Vβ7, which accounted for approximately 65% of the total signal. The normal range in blood for Vβ7 is 10–11%. There is clearly a preferential expansion of Vβ7+ CSF cells under the present culture conditions. Although several other Vβ bands can be seen, they account for a relatively small percentage of the total. The PBLs from this patient, like the others, is quite diverse, with no dominance noted. Table 7 shows the CDR3 domain of Vβ7 from patient 95 and demonstrates that a single cell arose during culturing.

The last sample, 101 was actually sorted for CD4 and ifs HLA DR positivity after culture but prior to PCR analysis. The CSF clearly contained 4–5 dominant Vβs. Interestingly, this was the first PBL sample to show a restricted profile which may be due to sorting the sample after culture.

Although a limited number of MS patients were examined it appears that Vβ7 is overrepresented in the CSF T cell population cultured with IL-2, IL-4, and Lymphocult.

Although the invention has been described with regard to present embodiments, the invention is not limited except by the claims.

We claim:

1. A composition for suppressing activity of T cells expressing Vβ6.2/3 T cell receptor in a human individual having multiple sclerosis, comprising an immunologically effective amount of a single chair peptide comprising an amino acid sequence of a peptide fragment of a non-constant region of a human Vβ6.2/3 T cell receptor chain, wherein said peptide fragment is identical in amino acid sequence to the amino acid sequence of a human Vβ6.2/3 T cell receptor chain, and a pharmaceutically acceptable medium.

2. A composition for suppressing activity of T cells expressing Vβ6.5 T cell receptor in a human individual having multiple sclerosis, comprising an immunologically effective amount of a single chain peptide comprising an amino acid sequence of a peptide fragment of a non-constant region of a human Vβ6.5 T cell receptor chain, wherein said peptide fragment is identical in amino acid sequence to the amino acid sequence of a human Vβ6.5 T cell receptor chain, and a pharmaceutically acceptable medium.

3. The composition of claim 2, wherein said peptide fragment comprises the amino acid sequence LGQGPEFLTYFQNEAQLEKS (SEQ ID NO:11).

4. A composition for suppressing activity of T cells expressing Vβ2 T cell receptor in a human individual having multiple sclerosis, comprising an immunologically effective amount of a single chain peptide comprising an amino acid sequence of a peptide fragment of a non-constant region of a human Vβ2 T cell receptor chain, wherein said peptide fragment is identical in amino acid sequence to the amino acid sequence of a human Vβ2 T cell receptor chain, and a pharmaceutically acceptable medium.

5. The composition of any of claims 1–3 or 4, further comprising an adjuvant.

6. The composition of claim 5, wherein said adjuvant is incomplete Freund's adjuvant (IFA).

7. The composition of any of claims 1–3 or 4, further comprising a second peptide comprising an amino acid sequence of a peptide fragment of a non-constant region of a second human T cell receptor chain selected from the group consisting of a Vβ6.2/3, a Vβ6.5, a Vβ2, a Vβ13, a Vβ5.1 and a Vβ7 chain, wherein said peptide fragment is identical in amino acid sequence to the amino acid sequence of a human Vβ6.2/3, Vβ6.5, Vβ2, Vβ13, Vβ5.1 or Vβ7 T cell receptor chain.

8. The composition of any of claims 1–3 or 4, wherein said composition comprises more than one peptide corresponding to different amino acid sequences of the same T cell receptor.

9. The composition of any of claims 1–3 or 4, wherein said peptide is conjugated to a carrier.

10. A method of suppressing activity of T cells expressing Vβ6.2/3 T cell receptor in an individual exhibiting or at risk of exhibiting multiple sclerosis, comprising administering to the individual the composition of claim 1.

11. A method of suppressing proliferation of T cells expressing Vβ6.2/3 T cell receptor in a human individual having multiple sclerosis, comprising administering to said individual an effective amount of a cytotoxic or cytostatic agent specifically reactive with human Vβ6.2/3, wherein said agent is an antibody.

12. A method of suppressing proliferation of T cells expressing Vβ6.5 T cell receptor in a human individual having multiple sclerosis, comprising administering to said individual an effective amount of a cytotoxic or cytostatic agent specifically reactive with human Vβ6.5, wherein said agent is an antibody.

13. A method of suppressing proliferation of T cells expressing Vβ13 T cell receptor in a human individual having multiple sclerosis, comprising administering to said individual an effective amount of a cytotoxic or cytostatic agent specifically reactive with human Vβ13, wherein said agent is an antibody.

14. A method of suppressing proliferation of T cells expressing Vβ2 T cell receptor in a human individual having multiple sclerosis, comprising administering to said individual an effective amount of a cytotoxic or cytostatic agent specifically reactive with human Vβ2, wherein said agent is an antibody.

15. The method of any of claims 11–14, wherein said antibody is attached to a radioactive or chemotherapeutic moiety.

16. A method of suppressing activity of expressing Vβ6.5 T cell receptor in an individual exhibiting or at risk of exhibiting multiple sclerosis, comprising administering to the individual the composition of claim 2.

17. A method of suppressing activity of T cells expressing Vβ6.5 T cell receptor in an individual exhibiting or at risk of exhibiting multiple sclerosis, comprising administering to the individual the composition of claim 3.

18. A method of suppressing activity of T cells expressing Vβ13 T cell receptor in an individual exhibiting or at risk of exhibiting multiple sclerosis, comprising administering to the individual a composition comprising an immunologically effective amount of a single chain peptide comprising an amino acid sequence of a peptide fragment of a non-constant region of a human Vβ13 T cell receptor chain, wherein said peptide fragment is identical in amino acid sequence to the amino acid sequence of a human Vβ13 T cell receptor chain, and a pharmaceutically acceptable medium.

19. A method of suppressing activity of T cells expressing Vβ2 T cell receptor in an individual exhibiting or at risk of exhibiting multiple sclerosis, comprising administering to the individual the composition of claim 4.

20. A method of suppressing activity of T cells expressing Vβ6.2/3, Vβ6.5, Vβ13 or Vβ2 T cell receptors in an individual exhibiting or at risk of exhibiting multiple sclerosis, comprising administering to the individual the composition of claim 7.

21. The method of any of claims 10 or 16–19, wherein said composition is administered more than once.

22. The method of any of claims 10 or 16–19, wherein said composition is administered in a formulation including an adjuvant.

23. The method of claim 22, wherein said adjuvant is IFA.

* * * * *